US010767037B2

(12) United States Patent
Maudens et al.

(10) Patent No.: US 10,767,037 B2
(45) Date of Patent: Sep. 8, 2020

(54) HYALURONIC ACID CONJUGATES AND USES THEREOF

(71) Applicant: UNIVERSITE DE GENEVE, Geneva (CH)

(72) Inventors: Pierre Maudens, Marle (FR); Eric Allemann, Troinex (CH); Olivier Jordan, Prangins (CH)

(73) Assignee: UNIVERSITE DE GENEVE, Geneva (CH)

( * ) Notice: Subject to any disclaimer, the term of this patent is extended or adjusted under 35 U.S.C. 154(b) by 81 days.

(21) Appl. No.: 16/094,559

(22) PCT Filed: Apr. 18, 2017

(86) PCT No.: PCT/EP2017/059213
§ 371 (c)(1),
(2) Date: Oct. 18, 2018

(87) PCT Pub. No.: WO2017/182483
PCT Pub. Date: Oct. 26, 2017

(65) Prior Publication Data
US 2019/0119486 A1    Apr. 25, 2019

(30) Foreign Application Priority Data
Apr. 19, 2016 (EP) .................................. 16166100

(51) Int. Cl.
| | |
|---|---|
| *C08L 51/02* | (2006.01) |
| *A61K 47/58* | (2017.01) |
| *C08J 3/075* | (2006.01) |
| *C08K 5/20* | (2006.01) |
| *A61L 27/20* | (2006.01) |
| *C08B 37/08* | (2006.01) |
| *C08K 5/3472* | (2006.01) |
| *A61K 47/69* | (2017.01) |

(52) U.S. Cl.
CPC .............. *C08L 51/02* (2013.01); *A61K 47/58* (2017.08); *C08B 37/0072* (2013.01); *C08J 3/075* (2013.01); *C08K 5/20* (2013.01); *C08K 5/3472* (2013.01); *A61K 47/6939* (2017.08); *A61L 27/20* (2013.01); *C08L 2203/02* (2013.01)

(58) Field of Classification Search
CPC ..... C08L 51/02; C08L 2203/02; A61K 47/58; A61K 47/6939; C08B 37/0072; C08J 3/075; C08K 5/20; C08K 5/3472; A61L 27/20
USPC ........................................................ 524/504
See application file for complete search history.

(56) References Cited

U.S. PATENT DOCUMENTS

2013/0171197 A1* 7/2013 Ho ...................... C12N 5/0068
424/400

FOREIGN PATENT DOCUMENTS

| WO | WO 2010/099818 | 9/2010 |
| WO | WO 2013/036847 | 3/2013 |
| WO | WO 2015/048988 | 4/2015 |

OTHER PUBLICATIONS

Brown, T. J. et al. "Turnover of Hyaluronan in Synovial Joints: Elimination of Labelled Hyaluronan From the Knee Joint of the Rabbit" *Experimental Physiology*, 1991, pp. 125-134, vol. 76.
Cooperstein, M. A. et al. "Assessment of cytotoxicity of (N-isopropyl acrylamide) and Poly(N-isopropyl acrylamide)-coated surfaces" *Biointerphases*, 2013, pp. 1-12, vol. 8, No. 19.
Coronado, R. et al. "Characterization of thermo-sensitive hydrogels based on poly(N-isopropylacrylamide)/hyaluronic acid" *Polymer Bulletin*, 2011, pp. 101-124, vol. 67.
Debets, M. F. et al. "Bioconjugation with Strained Alkenes and Alkynes" *Accounts of Chemical Research*, 2011, pp. 805-815, vol. 44, No. 9.
D'Este, M. et al. "Single step synthesis and characterization of thermoresponsive hyaluronan hydrogels" *Carbohydrate Polymers*, 2012, pp. 1378-1385, vol. 90.
Fraser, J. R. E. et al. "Hyaluronan: its nature, distribution, functions and turnover" *Journal of Internal Medicine*, 1997, pp. 27-33, vol. 242.
Global Innovation Healthcare Academy "HA pearls" Hong Kong, Aug. 29, 2018, p. 1.
He, C. et al. "In situ gelling stimuli-sensitive block copolymer hydrogels for drug delivery" *Journal of Controlled Release*, 2008, pp. 189-207, vol. 127.
Hiki, S. et al. "A Facile Synthesis of Azido-Terminated Heterobifunctional Poly(ethylene glycol)s for "Click" Conjugation" *Bioconjugate Chemistry*, 2007, pp. 2191-2196, vol. 18.
Iannitti, T. et al. "A new highly viscoelastic hyaluronic acid gel: rheological properties, biocompatibility and clinical investigation in esthetic and restorative surgery" *International Journal of Pharmaceutics*, 2013, pp. 583-592, vol. 456.
Jeon, O. et al. "Mechanical properties and degradation behaviors of hyaluronic acid hydrogels cross-linked at various cross-linking densities" *Carbohydrate Polymers*, 2007, pp. 251-257, vol. 70.
Kolb, H. C. et al. "Click Chemistry: Diverse Chemical Function from a Few Good Reactions" *Angewandte Chem. Int. Ed.*, 2001, pp. 2004-2021, vol. 40.
Lavertu, M. et al. "Heat-Induced Transfer of Protons from Chitosan to Glycerol Phosphate Produces Chitosan Precipitation and Gelation" *Biomacromolecules*, 2008, pp. 640-650, vol. 9, No. 2.
Lee, Y. et al. "Thermo-sensitive, injectable, and tissue adhesive sol-gel transition hyaluronic acid/pluronic composite hydrogels prepared from bio-inspired catechol-thiol reaction" *Soft Matter*, pp. 977-983, vol. 6.
Li, Z. et al. "Thermosensitive hydrogels for drug delivery" *Expert Opinion on Drug Delivery*, May 13, 2011, pp. 991-1007, vol. 8, No. 8.

(Continued)

*Primary Examiner* — William K Cheung
(74) *Attorney, Agent, or Firm* — Saliwanchik, Lloyd & Eisenschenk

(57) ABSTRACT

The present invention is directed to new graft polymer of a hyaluronic acid polymer and N-isopropylacrylamide based polymer, preparations, compositions and uses thereof. In particular, the invention relates to pH and/or thermo-sensitive compositions able to form spontaneously nanoparticles useful as active and agents and delivery systems for at least one bioactive agent.

24 Claims, 5 Drawing Sheets

(56) References Cited

OTHER PUBLICATIONS

Liu, L. et al. "Microbial production of hyaluronic acid: current state, challenges, and perspectives" *Microbial Cell Factories*, 2011, pp. 1-9, vol. 10, No. 99.

Liu, C. et al. "Strain-Promoted "Click" Modification of Mesoporous Metal—Organic Framework" *Journal of the American Chemical Society*, Oct. 31, 2012, pp. 18886-18888, vol. 134; Support Information, pp. S1-S31.

Maudens, P. et al. "Spontaneously formin nanoparticles of hyaluronic acid conjugates for joint lubrication and dermatological uses" 10th Innovation day of Geneva University Hospitals, Geneva Switzerland, 2016 (oral presentation), pp. 30-31.

Maudens, P. et al. "Recent advances in intra-articular drug delivery systems for osteoarthritis therapy" *Drug Discovery Today*, Dec. 2018, pp. 1-15.

Maudens, P. et al. "Self-assembled thermoresponsive nanostructures of hyaluronic acid conjugates for osteoarthritis therapy" *Nanoscale*, 2018, pp. 1845-1854, vol. 10.

Maudens, P. et al. "Self-Assembled Thermoresponsive Nanoparticles of hyaluronic acid conjugates for joint lubrication and dermatological uses" 44th Annual Meeting & Exposition of the Controlled Release Society, Boston, USA, 2017, p. 1.

Muramatsu, K. et al. "Biological Evaluation of Tissue-Engineered Cartilage Using Thermoresponsive Poly(N-isopropylacrylamide)-Grafted Hyaluronan" *Journal of Biomaterials and Nanobiotechnology*, 2012, pp. 1-9, vol. 3.

Ohya, S. et al. "Thermoresponsive Artificial Extracellular Matrix for Tissue Engineering: Hyaluronic Acid Bioconjugated with Poly(N-isopropylacrylamide) Grafts" *Biomacromolecules*, 2001, pp. 856-863, vol. 2, No. 3.

Pasale, S. K. et al. "Multiresponsive Hyaluronan-p(NiPAAm) "Click"-Linked Hydrogels" *Macromolecular Bioscience*, 2014, pp. 1025-1038, vol. 14.

Peroglio, M. et al. "Injectable Hyaluronan Hydrogels for Cell and Drug Delivery" *European Cells and Materials*, 2010, p. 1, vol. 20, Suppl. 1.

Peroglio, M. et al. "Injectable thermoreversible hyaluronan-based hyrdrogels for nucleus pulposus cell encapsulation" *European Spine Journal*, 2012, pp. S839-S849, vol. 21, Suppl. 6.

Pola, R. et al. "Click chemistry as powerful and chemoselective tool for the attachment of targeting ligands to polymer drug carriers" *Polymer Chemistry*, 2014, 1340-1350, vol. 5.

Robert, L. "Hyaluronan, a truly "youthful" polysaccharide. Its medical applications" *Pathologie Biologie*, 2015, pp. 32-34, vol. 63.

Schanté, C. E. et al. "Chemical modifications of hyaluronic acid for the synthesis of derivatives for a broad range of biomedical applications" *Carbohydrate Polymers*, 2011, pp. 469-489, vol. 85.

Takahashi, A. et al. "In Situ Cross-Linkable Hydrogel of Hyaluronan Produced via Copper-Free Click Chemistry" *Biomacromolecules*, 2013, pp. 3581-3588, vol. 14.

Takemoto, H. et al. "Acidic pH-Responsive siRNA Conjugate for Reversible Carrier Stability and Accelerated Endosomal Escape with Reduced IFNα-Associated Immune Response" *Angew. Chem. Int. Ed.*, 2013, pp. 6218-6221, vol. 52.

Tan, H. et al. "Thermosensitive injectable hyaluronic acid hydrogel for adipose tissue engineering" *Biomaterials*, Dec. 2009, pp. 1-23, vol. 30, No. 36.

Xu, J. et al. "Synthesis of Well-Defined Cyclic Poly(N-isopropylacrylamide) via Click Chemistry and Its Unique Thermal Phase Transition Behavior" *Macromolecules*, 2007, pp. 9103-9110, vol. 40, No. 25.

Written Opinion in International Application No. PCT/EP2017/059213, dated Jun. 21, 2017, pp. 1-6.

Na, K. et al., "Injectable Thermo-sensitive Hydrogels Blended Hyaluronic Acid including Transforming Growth Factors for Neocartilage Formation In Vivo Test," 2008, *Tissue Engineering and Regenerative Medicine*, pp. 482-487, vol. 5, No. 3.

\* cited by examiner

HYALURONIC ACID CONJUGATES AND USES THEREOF

CROSS-REFERENCE TO RELATED APPLICATION

This application is a U.S. National Stage entry under 35 U.S.C. § 371 based on International Application No. PCT/EP2017/059213, filed Apr. 18, 2017, which was published under PCT Article 21(2) and which claims priority to European Application No. 16166100.4, filed Apr. 19, 2016, which are all hereby incorporated in their entirety by reference.

FIELD OF THE INVENTION

The present invention relates to graft polymers of a hyaluronic acid polymer and N-isopropylacrylamide based polymer, preparations, compositions and uses thereof.

BACKGROUND OF THE INVENTION

Hydrogels for biomedical applications were developed extensively in the recent years.

They have become an important material of high interest due to their high water content, tissue-like elasticity and rather good biocompatibility.

Hydrogels are composed of hydrophilic homopolymer or copolymer networks and are able to swell in water or physiological fluids. Hyaluronic acid (HA), also called hyaluronan, or its salt sodium hyaluronate, is a natural and linear heteropolysaccharide polymer typically found in the connective and epithelial tissues of vertebrates with a molecular weight range of $10^5$-$10^7$ daltons. HA is composed of repeating disaccharide units of β-1, 3-N-acetyl glucosamine and β-1, 4-glucuronic acid with excellent viscoelasticity properties, high moisture retention capacity, and high bio compatibility (Lavertu et al., 2008, Biomacromolecules, 9, 640-65). Commonly, HA was extracted from rooster combs and currently it is essentially produced via microalgae or bacterial fermentation (Liu et al., 2011, Microb. Cell Fact., 10, 99). HA is suitable for a wide range of applications in medicine, cosmetics, and nutraceuticals (Fraser et al., 1997, J. Intern. Med., 242, 27-33; Robert, 2015, Pathol Biol, 63, 32-34). In particular, it is known for its role in the lubrication and homeostasis of cartilage. However, native HA does not persist for a long time in the human body and is cleared from the implant site because of its low retention capacity and its degradation due to the effect hyaluronidase (Brown et al., 1991, Exp. Physiol., 76, 125-134). Therefore, chemical modifications of HA, in particular cross-linking modifications, have been considered for efficient applications (Schante et al., 2011, Carbohydrate Polymers, 85, 469-489). pH or thermo-sensitive polymers were also synthesized, formulated and formed a hydrogel matrix (Na, 2008, Tissue Engineering and Regenerative Medicine, 5, 482-487; Coronado et al., 2011, Polymer Bulletin, 67, 101-124 and Lee et al., 2010, Soft Matter, 6, 977-983). However, these pH or thermo-sensitive polymers, due to their physicochemical properties, only form a gel matrix and do not provide an efficient cushioning effect. Furthermore, their residence time in vivo is still limited by the rapid enzymatic HA degradation.

Poly(N-isopropylacrylamide) (variously abbreviated in the literature pNiPAM, PNIPA, PNIPAAm, NIPA, PNIPAA or PNIPAm, also named after IUPAC poly[1-(isopropylcarbamoyl)ethylene], also named N-(1-Methylethyl)-2-propenamide homopolymer) is a highly pH or thermo-responsive polymer previously used to modify HA to impart pH or thermo-sensitivity (Schild, 1992, Progress in Polymer Science, 17, 163-249). pNiPAM represents a candidate with a good biocompatibility to introduce physical cross-links via association of hydrophobic domains and in situ forming hydrogel (Tan et al., 2009, Biomaterials, 30, 6844-6853; Cooperstein et al., 2013, Biointerphases, 8, 19). In the case of thermo-sensitive below the lower critical solution temperature (LCST) at about 32° C., the hydrophobic N-substituted groups of pNiPAM are hydrated by water molecules to form a homogeneous solution. Above LCST, hydrophobic interaction between the N-substituted groups increases and surpasses the water hydration energy, leading to aggregation of hydrophobic polymer chains and hydrogel formation (Guan et al., 2011, Expert Opinion on Drug Delivery, 8, 991-1007). Even though the pNiPAM monomer is non-biodegradable, it has been demonstrated that low molecular weights of pure pNiPAM chains are eliminated by renal clearance (He et al., 2008, Journal of Controlled Release, 127, 189-207). Thermo-reversible hyaluronic acid-poly(N-isopropylacrylamide) (HA-pNiPAM) hydrogels were already formulated for applications in multiple fields such as tissue engineering, drug delivery system, etc. and form a hydrogel matrix at body temperature similar to pure pNiPAM (Ohya et al., 2001, Biomacromolecules, 2, 856-863). In particular, thermo-reversible hyaluronan-poly(N-isopropylacrylamide) (HA-pNiPAM) hydrogels were synthesized through reversible addition-fragmentation chain transfer polymerization (RAFT) and "click" chemistry, through the functionalization of HA with alkyne groups and the reaction of the so-formed HA propargylamide with azido-terminated Poly(N-isopropylacrylamide) ($N_3$—PNIPAM) in presence of a chain transfer agent (CTA) and a copper-containing catalyst (WO 2010/099818; Mortisen et al., 2010, Biomacromolecules, 11, 1261-1272). Their degradation products were found cytocompatible to hTERT-BJ1 fibroblasts at $35 \times 10^3$ g·mol$^{-1}$ (Mortisen et al., 2010, supra). The disadvantages of these HA-pNiPAM gel matrixes lie in the fact that they do not provide long-term lubrication or cushioning effect and furthermore can contain residual copper.

Thus, there is a need to find HA-derived polymers that can provide a long residence time in the body at the injection site with appropriated biomechanical properties, while being well tolerated and easy to synthesize.

SUMMARY OF THE INVENTION

The present invention relates to the unexpected finding of HA graft polymers (HA-N-isopropylacrylamide based conjugates) which are graft polymers able to form spontaneously nanoparticles by a change in temperature and/or pH. Those new HA graft polymers comprise a linker molecule which is used to graft the N-isopropylacrylamide based polymer onto the HA, conferring to the graft polymer the ability to form nanoparticles by a change in temperature (above LCST) and/or pH, which represents a significant enhancement never reached before with pH and/or thermo-sensitive polymers. The present invention fulfils medical surgical and cosmetic needs in the field of tissue regeneration and may enable novel uses/applications in the field of drug delivery. Those new HA graft polymers are pH and/or thermo-sensitive polymer graft polymers which are injectable, stable, biocompatible and biodegradable with a long residence time in the body at the injection site due to the spontaneous nanoparticles formation with potential self-lubricating nano-ball-bearing (SLNBB) properties which can be used as a new viscosupplementation/lubrication material in medical or cosmetic applications.

An aspect of the invention provides a graft polymer of a hyaluronic acid and N-isopropylacrylamide based (HA graft polymer) according to the invention.

Another aspect of the invention relates to a pharmaceutical comprising at least one HA graft polymer according to the invention and at least one pharmaceutically acceptable carrier.

Another aspect of the invention relates to nanoparticles comprising an HA graft polymer according to the invention.

Another aspect of the invention relates to a cosmetic composition comprising at least one HA graft polymer according to the invention.

Another aspect of the invention relates to a hydrogel comprising at least one HA graft polymer of the invention.

Another aspect of the invention relates to a soft tissue filler comprising at least one HA graft polymer of a composition thereof according to the invention.

Another aspect of the invention relates to a method of preparation of an HA graft polymer, a composition thereof, a hydrogel, a soft tissue filler or nanoparticles thereof according to the invention.

Another aspect of the invention relates to an HA graft polymer according to the invention for use in in vivo drug delivery, in vitro cell or biological tissue culture and tissue engineering applications.

According to another particular embodiment, is provided a cell or biological tissue culture medium comprising an HA graft polymer or a composition thereof according to the invention.

According to another particular embodiment, is provided a reconstruction tissue comprising an HA graft polymer or a composition thereof according to the invention.

Another aspect of the invention relates to an HA graft polymer according to the invention for use in the prevention or treatment of a medical disorder, and in particular joint pathologies, articular diseases, eye pathologies, skin defects or injuries, urological tissue bulking, any tissue degeneration, enhancement/modification and/or increase of the volume of a body part for aesthetic or therapeutic reasons or for the treatment of a tumor or a vascular malformation.

Another aspect of the invention relates to a use of an HA graft polymer according to the invention for the preparation of a pharmaceutical formulation for the prevention or treatment of a medical disorder, and in particular joint pathologies, articular diseases, eye pathologies, skin defects or injuries, urological tissue bulking, and any tissue degeneration, enhancement/modification and/or increase of the volume of a body part for aesthetic, reconstructive or therapeutic reasons or for the treatment of a tumor or a vascular malformation.

Another aspect of the invention relates to a use of an HA graft polymer according to the invention for the preparation of a cell or biological culture medium or of a reconstruction tissue.

Another aspect of the invention relates to a method of preventing, treating or ameliorating a medical disorder selected from joint pathologies, articular diseases, eye pathologies, skin defects or injuries, urological tissue bulking and any tissue degeneration, a tumor or a vascular malformation in a subject, said method comprising administering to a subject in need thereof an effective amount of at least one HA graft polymer according to the invention or a pharmaceutical formulation thereof.

Another aspect of the invention relates to a kit comprising at least one graft polymer of the invention or composition thereof, e.g. in a lyophilized form.

Another aspect of the invention relates to a kit for preparation of nanoparticles for encapsulation of material, e.g. bioactive agent, drug substance, protein or antibody for prevention or treatment comprising at least one graft polymer of the invention or composition thereof.

DETAILED DESCRIPTION

Figure 1:
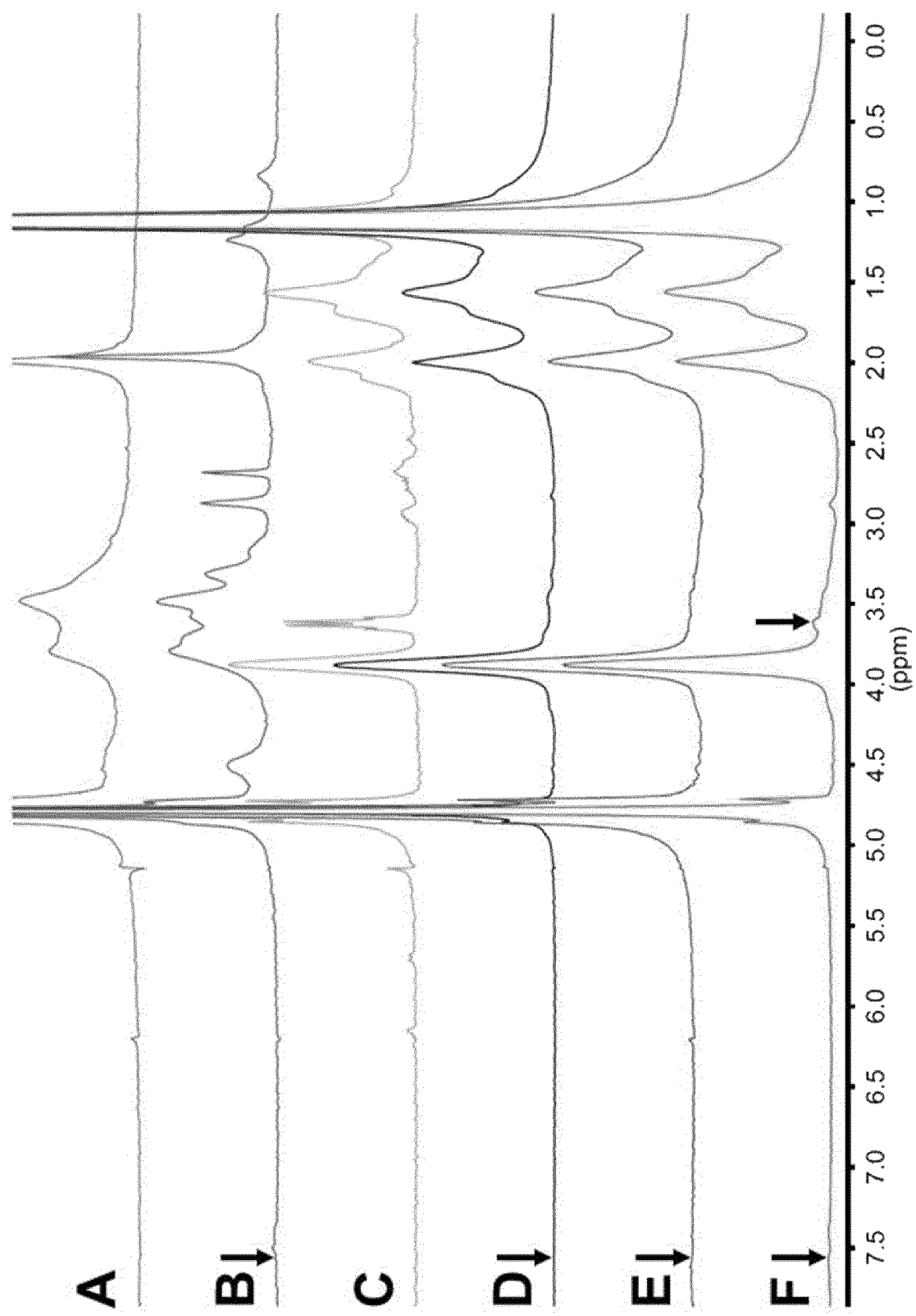
FIG. 1 shows the $^1$H NMR spectra in $D_2O$ of graft polymers of the invention D-F as compared to those of the starting material. A: Hyaluronic acid (HA), B: HA-DBCO, C: pNiPAM azide terminated, D: HA-B1, E: HA-B2 and F: HA-P2 as described in Example 1.

The term "polyethylene glycol (PEG) chain" refers to a chain comprising from two to about 5,000 ethylene glycol units, preferably 2 to 6 or 2 to 4 ethylene glycol units.

The term "hyaluronic acid" (HA) refers to linear heteropolysaccharide composed of D-glucuronic acid and D-N-acetylglucosamine, which are linked together via alternating β-1,4 and β-1,3 glycosidic bonds. Suitable HA polymers according to the invention encompass polysaccharides composed of up to 12,500 disaccharide repeats, and range in size from about 500 to 5,000,000 Da depending on the origin, in particular from about 500 to 3,000,000 Da. Each repeat unit bears a carboxylic chemical group on the D-glucuronic acid motif which can be potentially linked to form a graft polymer according to the invention. According to a particular aspect, the degree of substitution of those carboxylic groups with a linker of the invention is about 0.5-50%, typically from 2 to about 10%.

The term "degree of crosslink or substitution" as used herein means the quantity of pairs of functional groups converted into crosslinking or grafting bonds relative to the total quantity of pairs of functional groups initially present on the HA and the N-isopropylacrylamide based polymer, expressed as a percentage.

Suitable HA polymers according to the invention can be of various origins, including natural (generally animal), semi-synthetic or biotechnological (such as non-animal, produced by microorganism fermentation).

The term "N-isopropylacrylamide based polymer" includes all polymers named by IUPAC N-propan-2-ylprop-2-enamide (CAS number 2210.25.5). Suitable poly(N-isopropylacrylamide) polymers according to the invention include polymers having a molecular weight from about 500 to 35,000 Da, in particular from 2,000 to 25,000 Da.

The terms "conjugated" or "grafted" are used to indicate the formation of covalent bonds between HA and N-isopropylacrylamide based polymers leading to a graft polymer or conjugate of the invention, wherein such covalent bonding occurs through a linker according to the invention.

The term "click" chemistry refers to a variety of chemical reactions (e.g. azide-alkyne cycloadditions) that are characterized by their high yield, regioselectivity, stability, and ability to proceed without the generation of offensive byproducts as described in Kolb et al., 201, Chem. Int. Ed Engl., 40(11), 2004-2021. Importantly, these reactions can occur in a benign solvent, are insensitive to water and oxygen, and have a high thermo dynamic driving. The most common examples of these reactions are the carbon heteroatom bond formation resulting from cycloadditions of unsaturated species, nucleophilic substitution chemistry, non-aldol carbonyl chemistry, and additions to carbon-carbon multiple bonds. The graft polymers of the invention can be synthesized by click chemistry, and examples of synthetic routes are provided herein, which can be slightly adapted by the skilled person using standard knowledge.

The term "alkyl" when used alone or in combination with other terms, comprises a straight or branched chain of $C_1$-$C_{20}$ alkyl which refers to monovalent alkyl groups having 1 to 20 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refers respectively to monovalent alkyl groups having 1 to 9 carbon atoms, monovalent alkyl groups having 1 to 6 carbon atoms and monovalent alkyl groups having 1 to 4 carbon atoms.

Particularly, those include $C_1$-$C_6$ alkyl.

The term "$C_5$-$C_{10}$ cycloalkyl" refers to a saturated or unsaturated carbocyclic group of from 5 to 10 carbon atoms having a single ring such as C6-C8 cycloalkyl (e.g., cyclohexyl, cyclooctyl) or multiple condensed rings (e.g., norbornyl). C3-C8-cycloalkyl includes cyclopentyl, cyclohexyl, cyclopropyl, cyclobutyl, norbornyl and the like.

The term "heterocycloalkyl" refers to a $C_5$-$C_{10}$-cycloalkyl group according to the definition above, in which up to x carbon atoms are replaced by heteroatoms chosen from the group consisting of O, S, NR, R being defined as hydrogen or methyl. Heterocycloalkyl includes pyrrolidinyl, piperidinyl, piperazinyl, morpholinyl, tetrahydrofuranyl, azacyclooctyl and the like.

The term "C8 cycloalkyl" refers to a saturated or unsaturated carbocyclic group of 8 carbon atoms having a single ring (e.g., cyclooctyl) or multiple condensed rings (e.g., dibenzocyclooctynyl, mono fluorinated cyclooctyne, dibenzocyclooctyne, difluorocyclooctyne, biarylazacyclooctynone, cyclooctyne, dibenzoazacyclooctyne, nonfluorocyclooctyne, aryl-less cyclooctyne, bicyclononyne and dimethoxyazacyclooctyne) or those as described in Debets et al., 2011, Accounts for Chemical research, 44(9), 805-815.

The term "C8 heterocycloalkyl" refers to a C8 cycloalkyl group according to the definition above, in which up to 3 carbon atoms are replaced by heteroatoms chosen from the group consisting of O, S, NR, R being defined as hydrogen or methyl. C8 heterocycloalkyl include optionally substituted aza-dibenzocyclooctynyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "amino alkyl" refers to alkyl groups having an amino substituent, including 2-(1-pyrrolidinyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to alkyl groups having an aminocarbonyl substituent, including 2-(dimethylaminocarbonyl)ethyl, N-ethyl acetamidyl, N,N-diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "acyl" refers to the group —C(O)R where R includes H, "alkyl," preferably "$C_1$-$C_6$ alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "aryl $C_1$-$C_6$ alkyl," "heteroaryl $C_1$-$C_6$ alkyl," "$C_1$-$C_6$ alkyl cycloalkyl," "$C_1$-$C_6$ alkyl heterocycloalkyl," "amino," "amino sulfonyl," "ammonium," "acyl amino," "amino carbonyl," "aryl," "heteroaryl," "sulfinyl," "sulfonyl," "alkoxy," "alkoxy carbonyl," "carbamate," "sulfanyl," "halogen," trihalomethyl, cyano, hydroxy, mercapto, nitro, and the like.

The term "pharmaceutically acceptable" refers to a carrier comprised of a material that is not biologically or otherwise undesirable and not especially toxic.

The terms "biphasic hydrogel" is used herein to describe the state above the lower critical solution temperature (LCST), characterized by a suspension of condensed gel nanoparticles in a low-viscosity, gel-like continuous phase.

The terms "monophasic hydrogel" and "monophasic graft polymer solution" may be used interchangeably to describe a flowable monophasic state below the LCST.

According to one aspect of the invention, an HA graft polymer according to the invention undergoes a transition between a monophasic hydrogel and biphasic hydrogel at a LCST which is from about 25° C. to about 32° C., for example at body temperature.

The term "carrier" refers to any component present in a pharmaceutical formulation other than the active agent and thus includes diluents, binders, lubricants, disintegrants, fillers, coloring agents, wetting or emulsifying agents, pH buffering agents, preservatives and the like.

The term "bioactive agent" is used to describe any agent with biological activity to be incorporated into a graft polymer composition of the invention. It may be natural, synthetic, semi-synthetic or derivatives thereof and may include hydrophobic, hydrophilic, soluble and insoluble compounds. More specifically, it may be any bioactive agent useful for the treatment and/or prevention and/or diagnosis of conditions in any therapeutic area known in mammals, such as animals and humans, particularly humans, which include, but are not limited to inflammatory disease (including arthritis, osteoarthritis, and rheumatoid arthritis), eye pathologies, tumors and infections. The bioactive agents may be selected from a macromolecular compound or a small molecule compound, such as peptides, proteins, oligo- and poly-nucleotides, antibiotics, antimicrobials, growth factors, enzymes, antitumoral drugs, anti-inflammatory drugs, antiviral drugs, antibacterial, antifungal drugs, anaesthetics, anti-neoplastic drugs, analgesics, anticoagulants, haemostatic drugs and antibodies. More specifically, at least one bio active agent may be selected from the group consisting of corticosteroids and of p38 mitogen-activated protein kinases inhibitors.

The term "skin disorders" or "skin diseases" includes skin damages where the skin surface presents sore depression without necessarily a cut on its surface such as age-related tissue damages (e.g. wrinkles), wounds and scars such as for example acne or rubella scars. Those disorders further include wounds, scars, psoriasis, acne, eczema and rosacea. The term "wounds", includes any damaged tissue, for example following trauma or surgery. Wounds in mammals include for examples abrasions lacerations, contusions, concussions, stab wounds, skin cuts, surgical wounds, gunshot wounds, thermal wounds, chemical wounds, bites and stings and electrical wounds. It further includes chronic skin disorders such as ulcers.

The term "eye pathologies or disorders" are disorders or injuries that affect the eye and in particular the cornea. Such disorders include corneal abrasion, corneal scratches, corneal alkali burns, age-related macular degeneration, bulging eyes, cataracts, cytomegalovirus retinitis, color blindness, strabismus, diabetic macular edema, eye floaters and eye flashes, glaucoma, keratoconus, lazy eye, low vision, ocular hypertension, retinal detachment, eyelid twitching, uveitis, keratoconjunctivitis sicca (KCS) and dry eye syndrome.

The term "joint pathologies" includes osteoarthritis, arthritic pain, rheumatoid arthritis, infection and inflammation pain, traumatic knee events leading to cartilage, bone, ligament or synovial capsule damage.

The term "reconstruction tissue" refers to a biological tissue (endogenous or exogenous) or a synthetic or semi-synthetic material useful for repairing damaged tissues of the body such as epidermal, neurological, cartilage or bone tissues.

As used herein, "treatment" and "treating" and the like generally mean obtaining a desired pharmacological and/or physical and/or physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions such as improvement or remediation of damage.

The term "subject" as used herein refers to mammals. For examples, mammals contemplated by the present invention include human, primates, and domesticated animals such as cattle, sheep, pigs, horses and particularly race horses, laboratory rodents and the like.

The term "efficacy" of a treatment according to the invention can be measured based on changes in the course of disease in response to a use according to the invention. For example, the efficacy of a treatment according to the invention can be measured by a decrease of joint pain, improvement of lubrication of the joints, improvement of the mobility of the subject, improvement of the eye surface or reduced eye pressure.

Graft Polymers According to the Invention

According to one embodiment, a graft polymer of a hyaluronic acid polymer is provided and a N-isopropylacrylamide based polymer wherein the hyaluronic acid polymer and the N-isopropylacrylamide based polymer are conjugated through at least one linker L of Formula (II):

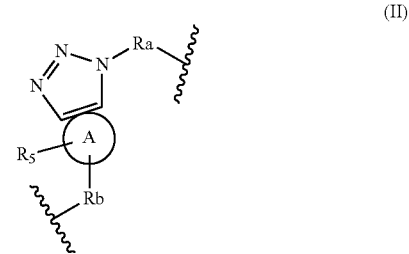

(II)

Wherein one of Ra and Rb is covalently linked to the N-isopropylacrylamide based polymer and one of one of Ra and Rb is covalently linked to the hyaluronic acid polymer and when Ra or Rb is covalently linked to the N-isopropylacrylamide based polymer, it is equal to $R^1$ and when Ra or Rb is covalently linked to the hyaluronic acid polymer, it is equal to $R^3$, wherein $R^1$ is a group selected from —$(CH_2)_x$—NH—$(CH_2)_y$—S—, —$(CH_2)_x$—NH—O—C(O)—$(CH_2)_y$—S—, —$(CH_2)_x$—NH—$(CH_2)_y$—C(O)—NH—$(CH_2)_z$—S—, —$(CH_2)_x$—O—C(O)—$CR^7R^8$—, —C(O)—$(CH_2)_x$—C(O)—NH—$(CH_2)_y$—S and a polyethylene glycol (PEG) chain wherein $R^7$ and $R^8$ are optionally substituted $C_1$-$C_6$ alkyl such as methyl; $R^3$ is a group -E-G-$L_1$- wherein E is either absent or selected from —C(O)—$NR^9$—, —C(O)—O— and —C(O)—, G is a linker group selected from optionally substituted $C_1$-$C_{20}$ alkyl such as ethyl, optionally substituted polyethylene glycol (PEG) chain, optionally substituted acylamino $C_1$-$C_6$ alkyl, optionally substituted acyl $C_1$-$C_6$ alkyl, optionally substituted aminocarbonyl $C_1$-$C_6$ alkyl and optionally substituted $C_1$-$C_6$ alkoxy and $L_1$ is selected from —$NR^{10}$C (O)—, —C(O)—NR$^{10}$—, —C(O)—O— and —C(O)—, wherein R$^9$ and R$^{10}$ are independently selected from H and optionally substituted C$_1$-C$_6$ alkyl such as methyl; A is an optionally substituted C$_5$-C$_{10}$-cycloalkyl, or optionally substituted heterocycloalkyl such as optionally substituted C8 cycloalkyl or optionally substituted C8 heterocycloalkyl ring wherein R$^5$ represents one or more substituent(s) independently selected from H, optionally substituted alkoxy such as methoxy and optionally substituted C$_1$-C$_6$ alkyl such as methyl; x, y and z are integers independently selected from 1 to 20 or any pharmaceutically acceptable salts thereof.

According to a particular embodiment, is provided an HA graft polymer of Formula (I):

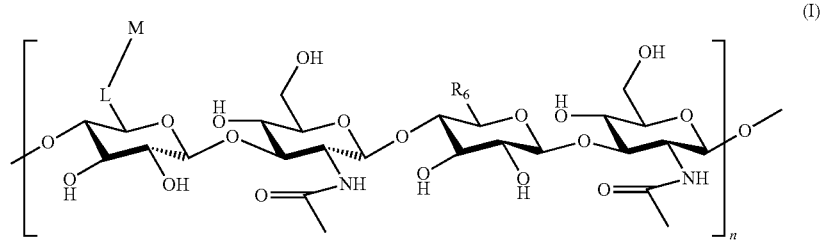

(I)

wherein M is a group selected from a moiety of Formula (M1) and of Formula (M2):

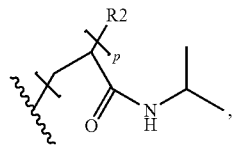

(M1)

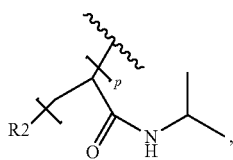

(M2)

R$^2$ is a group —B—(CH$_2$)$_i$-D, wherein B is either absent or selected from —S—C(S)—S— and —S—; D is a group selected from optionally substituted C$_1$-C$_{15}$ alkyl such as optionally substituted methyl, ethyl, butyl, propyl, hexyl, heptyl, octyl, nonyl, decanyl (e.g. optionally substituted C$_1$-C$_4$ alkyl such optionally substituted methyl or ethyl), optionally substituted alkoxycarbonyl C$_1$-C$_4$ alkyl, optionally substituted amino C$_1$-C$_4$ alkyl, optionally substituted aminocarbonyl C$_1$-C$_6$ alkyl, —COOH and —NH$_2$; p is an integer independently selected from 1 to 500; i is an integer independently selected from 0 to 500; R$^6$ is a group selected from —COOH and R$^3$, depending on the degree of substitution; L is a linker of Formula (II) as defined herein and n is an integer selected from 1 to 7,000 or any pharmaceutically acceptable salts thereof.

According to a particular embodiment, is provided a conjugate of Formula (I) wherein the linker L is linked to the HA moiety of the conjugate through its R$_b$ substituent.

According to a particular embodiment, is provided a conjugate of Formula (I) wherein the linker L is linked to the HA moiety of the conjugate through its R$_a$ substituent.

According to a particular embodiment, is provided a conjugate of Formula (I) wherein R$^1$ is a group —(CH$_2$)$_x$—O—C(O)—CR$^7$R$^8$— wherein R$^7$ and R$^8$ are optionally substituted C$_1$-C$_6$ alkyl such as methyl.

According to another particular embodiment, is provided a conjugate of Formula (I) wherein R$^1$ is a group —C(O)—(CH$_2$)$_x$—C(O)—NH—(CH$_2$)$_y$—S.

According to a particular embodiment, is provided a conjugate of Formula (I) wherein x is 3.

According to another particular embodiment, is provided a conjugate of Formula (I) wherein x is 2.

According to another particular embodiment, is provided a conjugate of Formula (I) wherein y is 2.

According to a further particular embodiment is provided an HA graft polymer of Formula (Ia):

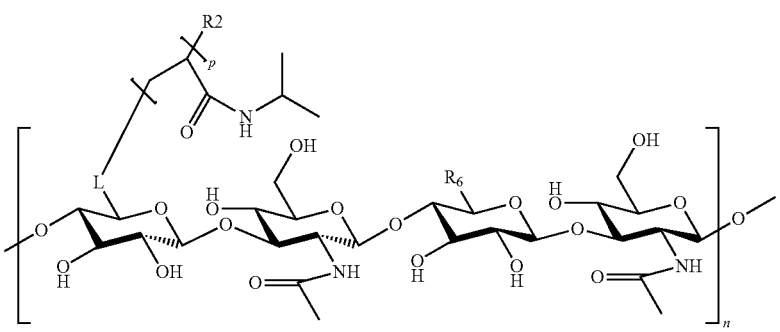

(Ia)

or any pharmaceutically acceptable salts thereof wherein L, R$^2$, R$^6$ and p are as described in the present description.

According to a particular embodiment, is provided a conjugate of Formula (I) wherein A is an optionally substituted C8 cycloalkyl or optionally substituted C8 heterocycloalkyl ring.

According to a further particular embodiment, is provided a conjugate of Formula (I) wherein A is an optionally substituted aza-dibenzocyclooctynyl.

According to a particular embodiment, is provided a conjugate of Formula (I) wherein p is from about 50 to 200.

According to a particular embodiment, is provided a conjugate of Formula (I) wherein $R^7$ and $R^8$ are optionally substituted $C_1$-$C_6$ alkyl, in particular methyl.

According to a particular embodiment, is provided a conjugate of Formula (I) wherein B is —S—C(S)—S—.

According to a particular embodiment, is provided a conjugate of Formula (I) wherein B is absent.

According to a particular embodiment, is provided a conjugate of Formula (I) wherein i is from 0 to 20, in particular 0 to 15 such as 0 to 11, in particular 11.

According to a particular embodiment, is provided a conjugate of Formula (I) wherein D is optionally substituted $C_1$-$C_4$ alkyl such as optionally substituted methyl (e.g. methyl optionally substituted by $C_1$-$C_{12}$ alkyl).

According to a particular embodiment, is provided a conjugate of Formula (I) wherein L is a group according to Formula (IIa):

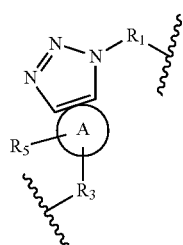

(IIa)

wherein A, $R^1$, $R^3$ and $R^5$ are as described herein.

According to a particular embodiment, is provided a conjugate of Formula (I) wherein L is a group according to Formula (IIb):

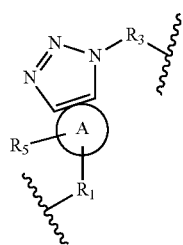

(IIb)

wherein A, $R^1$, $R^3$ and $R^5$ are as described herein.

According to a particular embodiment, is provided a conjugate of Formula (I) wherein L is a group according to Formula (II'):

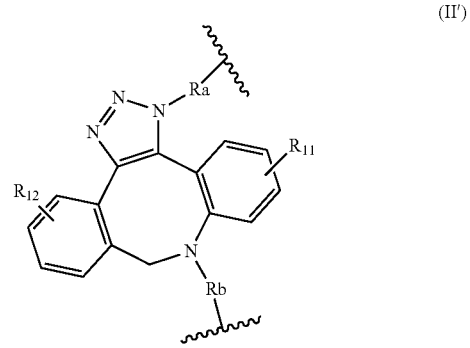

(II')

wherein $R^{11}$ and $R^{12}$ represent one or more substituent independently selected from H, optionally substituted alkoxy such as methoxy and optionally substituted $C_1$-$C_6$ alkyl such as methyl and Ra and Rb are as described herein.

According to a further particular embodiment, is provided a conjugate of Formula (I) wherein L is a group according to Formula (IIa'):

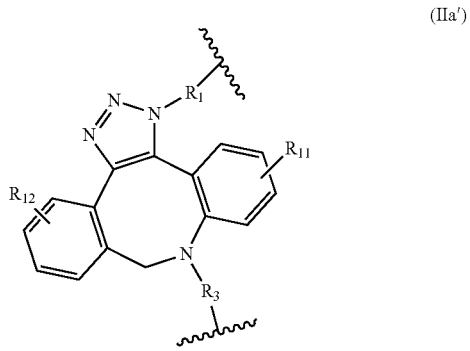

(IIa')

wherein $R^{11}$ and $R^{12}$ represent one or more substituent independently selected from H, optionally substituted alkoxy such as methoxy and optionally substituted $C_1$-$C_6$ alkyl such as methyl and $R^1$ and $R^3$ are as described herein.

According to another further particular embodiment, is provided a conjugate of Formula (I) wherein L is a group according to Formula (IIb'):

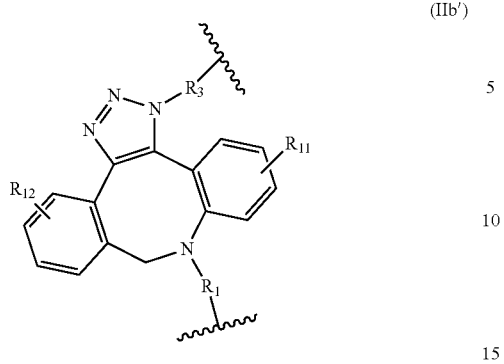

(IIb')

wherein $R^{11}$ and $R^{12}$ represent one or more substituent independently selected from H, optionally substituted alkoxy such as methoxy and optionally substituted $C_1$-$C_6$ alkyl such as methyl and $R^1$ and $R^3$ are as described herein.

According to a particular embodiment, is provided a conjugate of Formula (I) wherein $R^3$ is a group -E-G-$L_1$- as described herein wherein the linker group G is optionally substituted acylamino $C_1$-$C_6$ alkyl, in particular an acylamino $C_1$-$C_6$ alkyl group substituted with a PEG group, such as for example a group of the following formula: —$C_1$-$C_6$ alkyl-NH—C(O)—($CH_2$—$CH_2$—O)$_j$— $CH_2$—$CH_2$— wherein j is selected from 1 to 10, in particular 1 to 8 or 1 to 6 such as for example j is 1, 2, 3 or 4, in particular 4.

According to a particular embodiment, is provided a conjugate of Formula (I) wherein $R^3$ is a group -E-G-$L_1$- as described herein wherein the linker group G is $C_1$-$C_{20}$ alkyl such as methyl optionally substituted with an optionally substituted polyethylene glycol (PEG) chain, such as for example a group of the following formula: —$C_1$-$C_6$ alkyl-($CH_2$—$CH_2$—O)$_j$—O—$CH_2$— wherein j is selected from 1 to 10, in particular 1 to 8 or 1 to 6 such as for example j is 1, 2, 3 or 4, in particular 4.

According to a particular embodiment, is provided a conjugate of Formula (I) wherein $R^3$ is a group -E-G-$L_1$- as described herein wherein the linker group G is optionally substituted $C_1$-$C_{20}$ alkyl such as methyl.

According to a particular embodiment, is provided a conjugate of Formula (I) wherein $R^3$ is a group -E-G-$L_1$- as described herein wherein E is absent.

According to a particular embodiment, is provided a conjugate of Formula (I) wherein $R^3$ is a group -E-G-$L_1$- as described herein wherein E is —CO—.

According to a particular embodiment, is provided a conjugate of Formula (I) wherein $R^3$ is a group -E-G-$L_1$- as described herein wherein $L_1$ is —$NR^{10}C(O)$—.

According to a particular embodiment, $R^{10}$ is H.

According to a particular embodiment, is provided a conjugate of Formula (I) wherein L is a group according to Formulae (II), in particular (IIa') having the following Formula (II"):

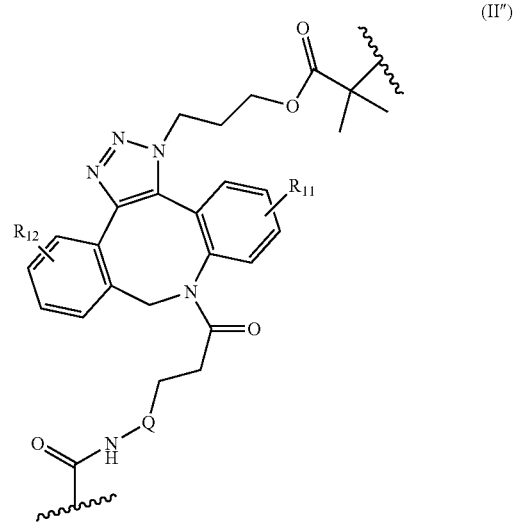

(II")

wherein Q is absent or a group of the following formula: —NH—C(O)—($CH_2$—$CH_2$—O)$_{1-4}$—$CH_2$—$CH_2$— and $R^{11}$ and $R^{12}$ are as described herein.

According to a particular embodiment, is provided a conjugate of Formula (I) wherein L is a group according to Formulae (II), in particular (IIb') having the following Formula (II'''):

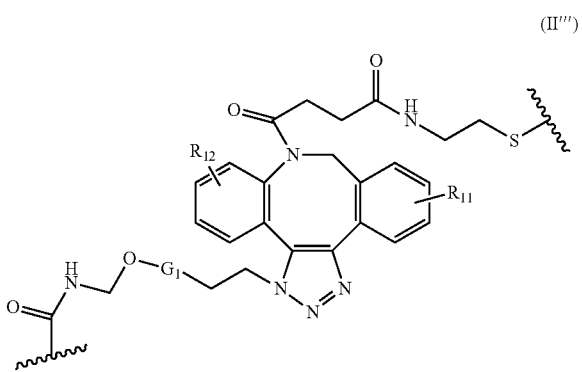

(II''')

wherein $G_1$ is a PEG and in a more particular embodiment a group of Formula: —($CH_2$—$CH_2$—O)$_{1-4}$— such as for example —($CH_2$—$CH_2$—O)$_2$— and $R^{11}$ and $R^{12}$ are as described herein.

According to a particular embodiment, $R^{11}$ and $R^{12}$ are H.

According to a particular embodiment, is provided a conjugate of Formula (I) selected from the following group:

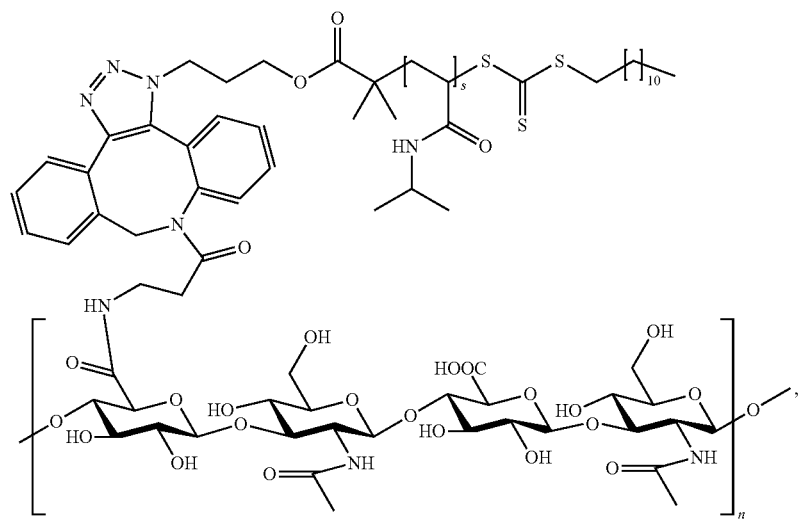
(HA-B1/HA-B2)
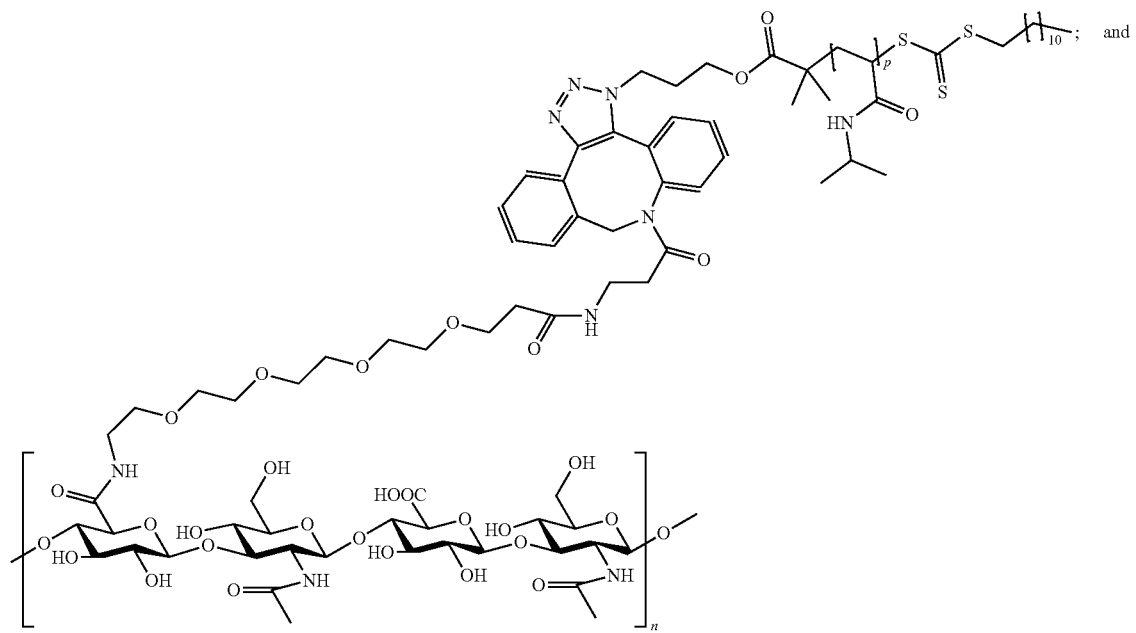
(HA-P2); and (HA-B3)

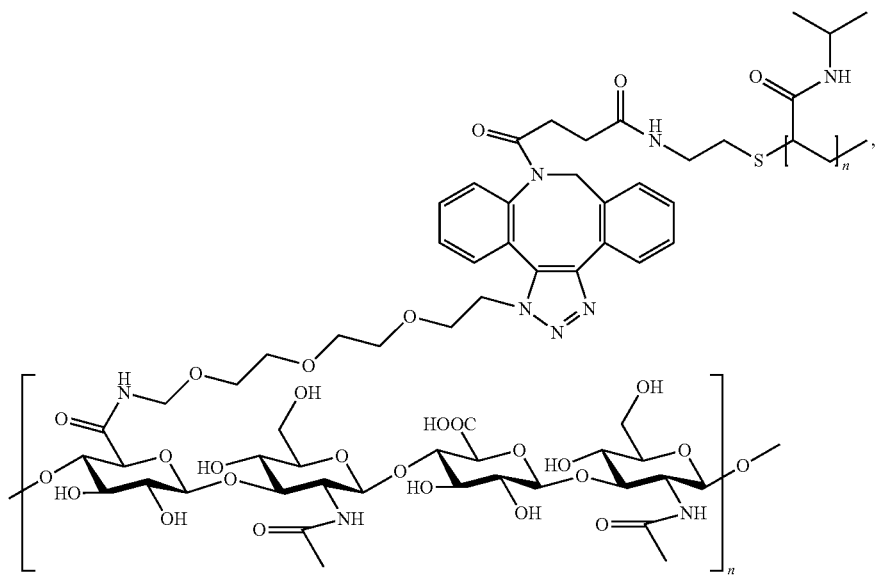

having a substitution degree between about 0.5 and 50, preferably about 2 and 10, or any pharmaceutically acceptable salts thereof.

According to a particular embodiment, pharmaceutically acceptable salts of conjugates of the invention comprise such as sodium, potassium, ammonium and calcium.

According to a particular embodiment, is provided a graft polymer of a hyaluronic acid polymer according to the invention wherein $R^3$ is a group -E-G-$L_1$- as defined herein wherein E is either absent.

According to another particular embodiment, is provided a graft polymer of a hyaluronic acid polymer according to the invention wherein $R^3$ is a group -E-G-$L_1$- as defined herein wherein E is —C(O)—.

According to another particular embodiment, is provided a graft polymer of a hyaluronic acid polymer according to the invention wherein $R^3$ is a group -E-G-$L_1$- as defined herein wherein G is an optionally substituted $C_1$-$C_{20}$ alkyl, for example selected from methyl, ethyl and propyl.

According to another particular embodiment, is provided a graft polymer of a hyaluronic acid polymer according to the invention wherein $R^3$ is a group -E-G-$L_1$- as defined herein wherein $L_1$ is —C(O)—O—.

According to another particular embodiment, is provided a graft polymer of a hyaluronic acid polymer according to the invention wherein $R^3$ is a group —O—(CH$_2$)—C(O)—O—.

According to another particular embodiment, is provided a graft polymer of a hyaluronic acid polymer according to the invention wherein $R^3$ is a group —(CH$_2$)$_3$—C(O)—O—.

It is understood that the molecular weight of the conjugate of the invention can be adapted in by the selection of the starting material and its choice will depend on the intended function of the graft polymer composition of the invention, formulation and hydrogel formed thereof. For example, the desired graft polymer composition degradation rate, the desired release rate of a bioactive agent optionally incorporated therein, the therapeutic condition to be treated will influence the choice of molecular weight for the conjugate of the invention.

In one embodiment, the molecular weight of graft polymers of the invention for use in lubricating/filler composition may be chosen between about 2,000 and about 250,000,000 Da, preferably from about 500,000 and about 10,000,000.

In another embodiment, the molecular weight of graft polymers of the invention for use in or as drug delivery system may be chosen between about 2,000 and about 250,000,000 Da, preferably from about 500,000 and about 10,000,000.

Preparation of Conjugates According to the Invention

The novel HA conjugates according to the invention can be prepared from readily available starting materials by using copper-free "click" chemistry and the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures. A general synthetic approach for obtaining conjugates of Formula (I) is to react an azide bearing N-isopropylacrylamide based polymer with an HA polymer bearing a cyclooctyne moiety or an azide bearing HA polymer with a N-isopropylacrylamide based polymer bearing a cyclooctyne moiety.

According to an aspect of the invention is provided a method for the preparation of a graft polymer of a hyaluronic acid polymer and N-isopropylacrylamide based polymer wherein the hyaluronic acid polymer and the N-isopropylacrylamide based are conjugated by at least one linker L of Formula (II), comprising the steps of:

(a) providing an HA polymer having at least one carboxylic acid group which is conjugated to at least one first functional group capable of participating in a "click chemistry" reaction;

(b) providing a N-isopropylacrylamide based polymer having at least one second complementary functional group capable of participating in a "click chemistry" reaction with the first functional group wherein said one of the functional groups is an azide moiety and the other functional group is an alkyne bearing precursor of the said linker L;

(c) reacting the at least one first functional group of the HA polysaccharide with the at least one second complementary functional group of the N-isopropylacrylamide based polymer via a "click chemistry" reaction to obtain a graft polymer composition of the invention; and (d) isolating the graft polymer composition.

According to a further particular embodiment, a method of the invention may comprise further steps of physically dispersing and/or covalently linking and/or adding at least one bioactive agent in the graft polymer composition obtained in step d).

A general synthetic approach for obtaining conjugates of Formula (I), in particular of Formula (Ic1) is illustrated in Scheme 1 below. HA conjugates according to Formula (I), whereby $R^1$, $R^2$, $R^3$, $R^5$, $R^6$ and p are defined in the detailed description, may be prepared in one single chemical step by click chemistry in an appropriate solvent such as for example a water-DMSO mixture at a volume ratio of 1:1, from custom made or commercially available starting materials.

The intermediate (Ia1) might be commercially available or prepared by reacting a compound wherein one of the functional groups is an azide moiety with N-isopropylacrylamide based polymer by amidation, esterification, thioetherification, oxidation or Ugi condensation.

The intermediate (Ib1) might be commercially available or prepared by reacting the linker precursor of Formula (Lprec1) with hyaluronic acid or any pharmaceutically acceptable salts thereof by amidation, esterification, thioetherification or maleimide-sulfhydryl reaction, oxidation or Ugi condensation such as described in Schanté et al., 2011, *Carbohydrate Polymers*, 85, 469-489.

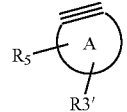

(L prec1)

wherein A and $R_5$ are as defined herein and $R_3'$ is a group -E-G-$L_1'$ wherein E and G are as defined herein and $L_1'$ is an amino group.

Scheme 1

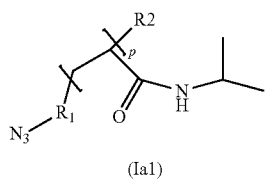

(Ia1)

+

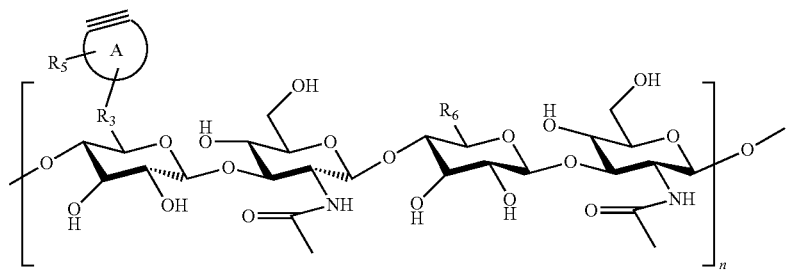

(Ib1)

↓

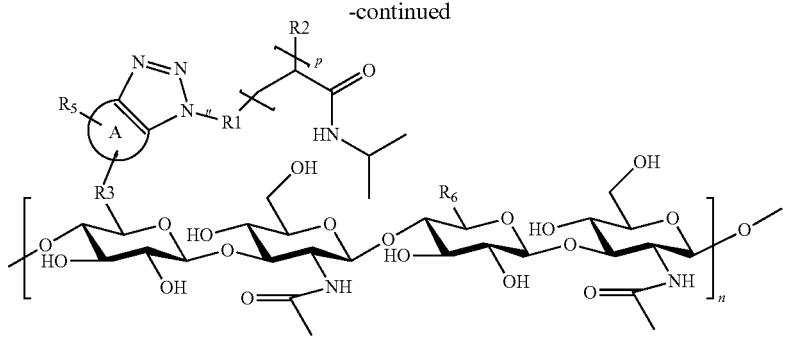
(Ic1)
Another general synthetic approach for obtaining conjugates of Formula (I), in particular of Formula (Ic2), is depicted in Scheme 2 below in one single chemical step by click chemistry in an appropriate solvent such as water and/or dimethyl sulfoxide, etc., from custom made or commercially available starting materials.
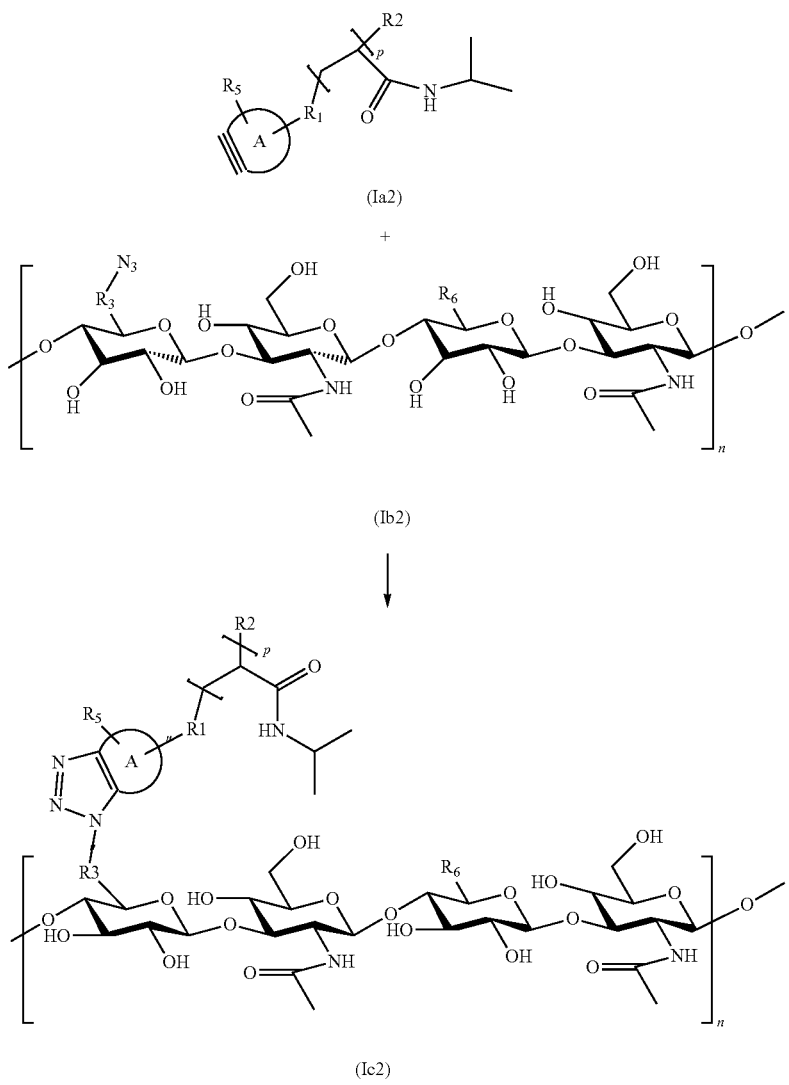
Scheme 2
(Ia2)
+
(Ib2)
↓
(Ic2)

The intermediate (Ia2) might be commercially available or prepared by reacting the linker precursor of Formula (Lprec2) with N-isopropylacrylamide based polymer by amidation, esterification, thioetherification, oxidation or Ugi condensation.

(L prec2)

wherein A and $R_5$ are as defined herein and $R_1'$ is an alcohol, carboxylic acid, carbonyl, azide, thioester, maleimide, acyl phosphate, acid anhydride, acyl chloride, carboxylate amino or ester group.

The intermediate (Ib2) might be commercially available or prepared by reacting a compound wherein one of the functional groups is an azide moiety with hyaluronic acid or any pharmaceutically acceptable salts by amidation, esterification, thioetherification, oxidation or Ugi condensation.

According to a particular embodiment, is provided an intermediate (Ia2)

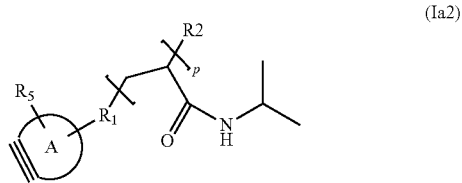

(Ia2)

wherein A, $R^1$, $R^2$, $R^5$ and p are as defined herein.

Compositions

The invention provides pharmaceutical or therapeutic agents as compositions, or medical devices comprising thereof and methods for treating a subject, preferably a mammalian patient, and most preferably a human patient who is suffering from a medical disorder, and in particular joint pathologies, articular diseases, eye pathologies (such as age-related macular degeneration, bulging eyes, cataracts, cytomegalovirus retinitis, color blindness, strabismus, diabetic macular edema, eye floaters and eye flashes, glaucoma, keratoconus, lazy eye, low vision, ocular hypertension, retinal detachment, eyelid twitching and uveitis), skin defects or injuries (such as wounds, scars, psoriasis, acne, eczema and rosacea) and from any tissue degeneration (such as stress urinary incontinence, systemic lupus erythematosus, rheumatoid arthritis, scleroderma, sjögren's syndrome, mixed connective tissue disease, psoriatic arthritis, marfan syndrome, peyronie's disease, ehlers-Danlos syndrome, osteogenesis imperfecta, stickler syndrome, alport syndrome, congenital contractural arachnodactyly, Loeys-Dietz syndrome and scurvy).

In a particular embodiment, the invention provides a pharmaceutical formulation comprising at least one conjugate or composition according to the invention for use as a medicament.

In another particular embodiment, compositions of the invention are parenteral formulations.

In a particular embodiment, compositions of the invention are injectable formulations, such as intra-articular, intra-arterial, intravenous, intrasynovial, intradermal, subdermal, submucosal, interstitial and intramuscular formulations.

In another particular embodiment, compositions of the invention are oral formulations.

In another particular embodiment, compositions of the invention are topical formulations.

In another particular embodiment, compositions of the invention are ophthalmic formulations.

Alternatively the invention provides compositions that can be used in another mammal thus humans for the same uses as described above.

The invention further provides compositions or medical devices useful for cosmetic applications, reconstruction surgery (e.g. tissue reconstruction) and cell or biological tissue culture (e.g. stem cell culture). Those compositions further comprise respectively cosmetically acceptable carriers or cell or biological tissue culture nutrients.

Compositions according to the invention comprise soft tissue filler compositions, for example, dermal and subdermal fillers, comprising at least one conjugate of the invention or hydrogel or nanoparticles thereof. Preparation of HA-based soft tissue filler compositions are well known to the skilled person and can be carried out for example as described in Jeon et al., 2007, Carbohydrate Polymers, 2007. 70(3): p. 251-257, Iannitti et al, 2013, Int. J. Pharm., 456:583-592.

According to a particular embodiment, compositions of the invention have a viscosity of between about 0.001 Pa*s and about 100 Pa*s and preferably from about 0.1 to 10 Pa·s when measured at about 100 Hz in oscillating mode at 20° C.

According to a particular embodiment, compositions of the invention have an extrusion force between about 0.01 N and about 20 N and preferably from about 1 N and about 5 N at 25° C. with an extrusion rate of about 1 mm/minute through a 29 Gauge needle.

According to a particular embodiment, upon solubilization in an aqueous solvent, graft polymer compositions of the invention may form a pH and/or thermo-sensitive hydrogel showing a monophasic-to-biphasic phase transition with temperature change.

According to a particular aspect, graft polymer compositions of the invention form a monophasic hydrogel and "monophasic graft polymer solution" below LCST which as below from about 25° C. to about 32° C. According to another particular aspect, graft polymer compositions of the invention form a biphasic hydrogel above such lower critical solution temperature.

In particular embodiment, graft polymer compositions of the invention may spontaneously form nanoparticles above from about 25° C. to about 32° C., for example at body temperature.

Further, the graft polymer compositions of the invention present the advantage to undergo this nanoparticle formation which is reversible and therefore potential temperature effects during storage and transport would not affect irreversibly the physical state of the polymer.

In particular embodiment is provided nanoparticles of graft polymer compositions of the invention having a mean size ranging from about 40 and 500 nm.

According to another particular embodiment, compositions of the invention can be in the form of a pH and/or thermo-reversible hydrogel which is biodegradable and biocompatible. In particular, compositions of the invention may be in the form of a pH and/or thermo-reversible biodegradable hydrogel which is in monophasic (solution or liquid) state at or around room temperature or lower and in a gelled state at or around physiological (or in vivo) temperature or higher.

Compositions of this invention may further comprise one or more pharmaceutically acceptable additional ingredient(s) such as alum, stabilizers, antimicrobial agents, buffers, coloring agents, flavoring agents, adjuvants, and the like.

The compositions according to the invention, together with a conventionally employed adjuvant, carrier, diluent or excipient may be placed into the form of pharmaceutical compositions and may be employed as solids, such as tablets or filled capsules, or liquids such as solutions, suspensions, ointments, emulsions, elixirs, or capsules filled with the same, films or gels, all for oral use. The compositions may also be formulated as a dry product for reconstitution with water or another suitable vehicle before use.

Compositions of this invention as liquid formulations including, but not limited to, aqueous or oily suspensions, solutions, emulsions, syrups, and elixirs.

Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Further materials as well as formulation processing techniques and the like are set out in *The Science and Practice of Pharmacy* (Remington: *The Science & Practice of Pharmacy*), 22$^{nd}$ *Edition*, 2012, *Lloyd, Ed. Allen, Pharmaceutical Press*, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycolate. Wetting agents include, but are not limited to, sodium lauryl sulfate. Tablets may be coated according to methods well known in the art.

In another particular embodiment, the compositions or hydrogels of the invention further comprise a bio active agent, which is either dispersed in or covalently attached to the graft polymer composition.

In another particular embodiment, the compositions or hydrogels of the invention are in the form of a bioactive agent delivery system.

In one embodiment the at least one bioactive substance may be present in an amount of between about 0.001 to 40 wt %, preferably about 0.01 to 30 wt % based on the total amount of the graft polymer composition or the hydrogel of the invention.

According to another aspect, compositions according to the invention comprise a cell or biological tissue culture medium comprising an HA graft polymer or a composition thereof. This culture medium may further comprise cell nutrients such as glucose, vitamins, growth factors, metal ions and the like.

According to another aspect, compositions according to the invention comprise a biological tissue (endogeneous or exogeneous) or a synthetic or semi-synthetic material useful for repairing damaged tissues of the body such as epidermal, neurological, cartilage or bone tissues.

In another particular embodiment, is provided a method of preparation of a culture medium comprising a step of mixing an HA graft polymer according to the invention with cell culture nutrients such as glucose, vitamins, growth factors, metal ions and the like.

In another particular embodiment, is provided a method of preparation of a reconstruction tissue comprising a step of combining an HA graft polymer or a composition thereof according to the invention with materials, tissues or cells useful for repairing damaged tissues of the body such as stem cells or epidermal, neurological, cartilage or bone tissues.

In another particular embodiment, is provided a method of preparation of a graft polymer composition, or hydrogel of the invention, in particular a delivery system for an active principle comprising the steps of:
  Providing a graft polymer or a composition thereof or hydrogel of the invention in gel state;
  Providing an active principle to be delivered;
  Mixing the said graft polymer or composition thereof or hydrogel of the invention with the said active principle (e.g. drug);
  Optionally inducing formation of nanoparticles by increasing the temperature to the mixture (typically from about 25 to about 40° C.);
  Collecting the so-obtained composition, hydrogel or nanoparticles loaded with the active principle (e.g. drug).

According to a particular aspect, compositions, hydrogels, or nanoparticles of the invention can be useful, once loaded with an active principle, for administration and in situ release of the said active principle injection.

Mode of Administration

Compositions of this invention may also be administered in any manner by injection such as subcutaneous injections, intra-synovial, intra-arterial, intravenous, intraarticular, intramuscular, subdermal, submucosal and interstitial injections.

Compositions of this invention may also be administered in any manner by injection such as subcutaneous injections, intra-synovial, intra-arterial, intravenous, intraarticular, intramuscular, subdermal, submucosal and interstitial injections Compositions of this invention may also be administered topically to the skin, various mucous or the eye.

Combination

According to one aspect, polymers of the invention or any suitable pharmaceutically acceptable thereof and pharmaceutical formulations thereof may be administered alone or in combination with at least one co-agent.

According to a particular aspect, co-agents according to the invention include pure HA, chondroitin sulfate or another intra-articular drug composition as well as bioactive agents according to the invention.

The invention encompasses the administration of conjugates of the invention and pharmaceutical formulations thereof to an individual simultaneously or sequentially with at least a co-agent useful in the treatment of inflammatory disease (including arthritis, osteoarthritis, and rheumatoid arthritis), eye pathologies, tumors and infections. Those co-agents can be selected from antibiotics, antimicrobials, growth factors, enzymes, antitumoral drugs, anti-inflammatory drugs such as corticosteroids, antiviral drugs, antibacterial, antifungal drugs, anaesthetics, anti-neoplastic drugs, analgesics, anticoagulants and haemostatic drugs.

Polymers, nanoparticles or hydrogel of the invention or a pharmaceutical formulation thereof that is administered simultaneously with said co-agent can be administered in the same or different composition(s) and by the same or different route(s) of administration.

The concentration range of a polymer of the invention, nanoparticles or hydrogel thereof in compositions of the invention may vary depending on the circumstances of each case, the underlying disease, the clinical indication and the desired intensity of pain relief which is aimed at and/or necessary.

According to one embodiment, is provided a pharmaceutical formulation comprising at least one conjugate of the invention or any suitable pharmaceutically acceptable thereof combined with at least one co-agent described herein, and at least one pharmaceutically acceptable carrier.

The dosage administered, as single or multiple doses, to an individual will vary depending upon a variety of factors, including pharmacokinetic properties, patient conditions and characteristics (sex, age, body weight, health, and size), extent of symptoms, concurrent treatments, frequency of treatment and the effect desired.

Patients

In an embodiment, patients according to the invention are subjects suffering or at risk of suffering from any tissue degeneration, articular diseases, eye pathologies, skin defects or injuries.

In a further embodiment, patients according to the invention are subjects suffering or at risk of suffering from joint pathologies and articular diseases such as osteoarthritis, arthritis, infection, rheumatoid arthritis and traumatic knee events leading to cartilage, bone, ligament or synovial capsule damage.

In another further embodiment, patients according to the invention are subjects suffering or at risk of suffering from eye pathologies such as age-related macular degeneration, bulging eyes, cataracts, cytomegalovirus retinitis, color blindness, strabismus, diabetic macular edema, eye floaters and eye flashes, glaucoma, keratoconus, lazy eye, low vision, ocular hypertension, retinal detachment, eyelid twitching and uveitis.

In another further embodiment, patients according to the invention are subjects suffering or at risk of suffering from skin defects or injuries such as scars, abrasions lacerations, contusions, concussions, stab wounds, skin cuts, surgical wounds, gunshot wounds, thermal wounds, chemical wounds, bites and stings and electrical wounds. It further includes chronic skin disorders such as ulcers.

In another further embodiment, patients according to the invention are subjects willing or requiring body parts volume enhancements or anatomical reshapes such as urological tissue bulking, any enhancement/modification and/or increase of the volume of a body part for aesthetic or therapeutic reasons.

In another further embodiment, patients according to the invention are subjects suffering from a tumor or a vascular malformation.

Use According to the Invention

According to a particular embodiment, the HA conjugates of the invention and compositions thereof are useful for various applications such as in vitro cell or biological tissue culture, as tissue fillers, for cosmetic, and tissue engineering applications.

According to another particular embodiment, is provided a use of a graft polymer or a hydrogel or a nanoparticle according to the invention for the preparation of a delivery system, in vitro cell or biological tissue culture or of tissue engineering materials, such as neurosurgical, bone, cartilage, epidermal reconstruction tissues.

According to another particular embodiment, the HA conjugates of the invention and compositions thereof are useful for use in the prevention or treatment of a medical disorder, and in particular joint pathologies, articular diseases, eye pathologies, skin defects or injuries, urological tissue bulking, any tissue degeneration, enhancement/modification and/or increase of the volume of a body part for aesthetic or therapeutic reasons or for the treatment of a tumor or a vascular malformation.

According to a further particular embodiment, formulations of the invention can be used under monophasic hydrogel form, below LCST for injecting into the capillary bed of a tumor or a vascular malformation, wherein said formulations form in situ small hydrogel particles upon exposure to body temperature (above LCST), thereby allowing vascular embolization. The resulting embolization of the said tumor or vascular malformation results in the blocking of blood and nutrients access and would be useful in either directly killing the tumor or for the preparation of a further surgical resection or treatment, such as in combination with radiotherapy or chemotherapy.

According to a further particular aspect of the invention, is provided an HA conjugate of the invention and compositions thereof for use in vascular embolization.

According to another further particular aspect, is provided an HA conjugate of the invention and compositions thereof for cosmetic use and for aesthetic and reconstructive surgery.

According to another further particular aspect, is provided an HA conjugate of the invention and compositions thereof for use in in vivo drug delivery.

According to a particular embodiment, is provided a pH and/or thermo-sensitive biodegradable hydrogel comprising at least one HA conjugate of the invention which is useful in many medical applications such as delivery system for at least one bioactive agent or cell delivery system in tissue engineering, cell or biological tissue culture systems, and the like.

According to a particular aspect, is provided the use of a hydrogel according to the invention as a delivery system for at least one bioactive agent.

In another embodiment of the invention is provided a use of at least one HA conjugate of the invention or any suitable pharmaceutically acceptable composition thereof alone in combination with at least one co-agent for the preparation of a pharmaceutical formulation for the prevention or treatment of tissue degeneration and related disorders.

According to a particular aspect, is provided an HA conjugate of the invention and compositions thereof wherein said conjugate is able to form in situ spontaneously nanoparticles.

Examples illustrating the invention will be described hereinafter in a more detailed manner and by reference to the embodiments represented in the Figures.

EXAMPLES

The following abbreviations refer respectively to the definitions below: DMSO (dimethyl sulfoxide), MWCO (Molecular weight cut-off).

Example 1: Synthesis of Hyaluronic Acid Conjugates of the Invention

Conjugates of the invention were synthesized as described in Scheme 1 above, wherein the starting materials (linker precursors) used for building the linkers were: Dibenzocyclooctyne-Amine (DBCO-amine) (Formula (L-prec1) wherein A is a C8 heterocyloalkyl ring being dibenzocylooctyne, $R^5$ is H and $R^{3'}$ is a -E-G-$L_1'$ group wherein E is —C(O)—, G is ethyl and $L_1'$ is —$NH_2$) purchased from Sigma-Aldrich (St. Louis, USA). Dibenzocyclooctyne-$PEG_4$-Amine (DBCO-$PEG_4$-amine) Formula (L-prec1) wherein A is a C8 heterocyloalkyl ring being dibenzocylooctyne, $R^5$ is H and $R^{3'}$ is a -E-G-$L_1'$ group wherein E is —C(O)—, G is —NH—C(O)—($CH_2$—$CH_2$—O$)_4$—$CH_2$—$CH_2$— and $L_1'$ is —$NH_2$) purchased from Click Chemistry Tools (Scottsdale, Ariz., USA).

Alternatively, the linker precursors DBCO-amine and DBCO-$PEG_4$-amine can be prepared as described in Pola et al., 2014, *Polym. Chem.*, 5, 1340 and the Poly(N-isopropylacrylamide) azide terminated (pNiPAM-$N_3$) can be prepared as described by Xu et al., 2007, *Macromolecules*, 40, 9103-9110.

Azido-$PEG_3$-Amine ($N_3$—$PEG_4$-amine) purchased from Click Chemistry Tools (Scottsdale, Ariz., USA).

Dibenzocyclooctyne-NHS Ester (DBCO-NHS Ester) (Formula (L-prec2) wherein A is a C8 heterocyloalkyl ring being dibenzocylooctyne, $R^5$ is H and $R^{1'}$ is a -E-G-$R^{1'}$ group wherein E is —C(O)—, G is ethyl and $R^{1'}$ is —COOH activated with N-hydroxysuccinimide/ethyl(dimethylaminopropyl) carbodiimide (NHS/EDC)).

Alternatively, the linker precursors $N_3$-$PEG_4$-amine can be prepared as described by Hiki et al., 2007, *Bioconjugate Chem.*, 18, 2191-2198 and DBCO-NHS Ester can be prepared as described in Liu et al., 2012, *J. Am. Chem. Soc.*, 134, 18886-18888. The further starting materials used are the following:

Hyaluronic Acid (HA) was purchased from Soliance (Pomacle, France) (MW: 1.85 MDa); N-(3-dimethylaminopropyl)-N'-ethylcarbodiimide hydrochloride (EDC), N-hydroxysuccinimide (NHS), Poly(N-isopropylacrylamide) azide terminated (pNiPAM-$N_3$) (MW: 15 kDa) (Formula (Ia1) wherein R' is as described in the detailed description with x being 3, $R^7$ and $R^8$ are methyl, p is 132 and $R^2$ is as described in the detailed description with B being —S—C(S)—S—, i being 11 and D being methyl) and Poly(N-isopropylacrylamide) amine terminated (pNiPAM-amine) were purchased from Sigma-Aldrich (St. Louis, USA). Cyanine5-azide (Cy5-$N_3$) was provided by Lumiprobe (Hannover, Germany).

Synthesis of HA-B1

The title conjugate of the invention was synthesized according to Scheme 1A below. HA (1) is dissolved in distilled water at 1% (w/v). After the dissolution of the polymer, EDC was added (1 eq. COO$^-$) and 5 min latter NHS was dissolved (1 eq.) under magnetic stirring (5 min at 1,200 RPM). The pH was adjusted to 5.0 with a pH gel electrode Metrohm (Herisau, Switzerland) with NaOH/HCl 0.1M. DBCO-amine (2) was used as a precursor of Formula (Lprec1) as defined above and was added (1 eq.) with DMSO for a final volume ratio 40:60 of water-DMSO mixture. The reaction was stirred overnight at room temperature and was precipitated in ethanol to obtain intermediate of Formula (Ib1) wherein A is a C8 heterocyloalkyl ring being dibenzocylooctyne, $R^5$ is H and $R^3$ is —C(O)—($CH_2)_2$—NH—C(O)— (3). The precipitate (3) was lyophilized, re-dissolved in distilled water at 1% (w/v) and pNiPAM-N3 (1 eq.) (4) used as intermediate of Formula (Ia1) as described above was added (2 h at 1,200 RPM). HA-P1 was dialyzed (MWCO 25,000, Spectra/Por® membrane, Rancho Dominguez, USA) against NaCl 5% (w/v) in distilled water 3 times during 3 h at 1,500 RPM and was precipitated in ethanol and lyophilized and stored at 4° C.

The structure of the resulting conjugate of the invention HA-B1 was determined by 1H NMR Gemini 300 MHz from Varian (Grenoble, France) spectra (FIG. 1D) at ambient temperature using $D_2O$ as a solvent.

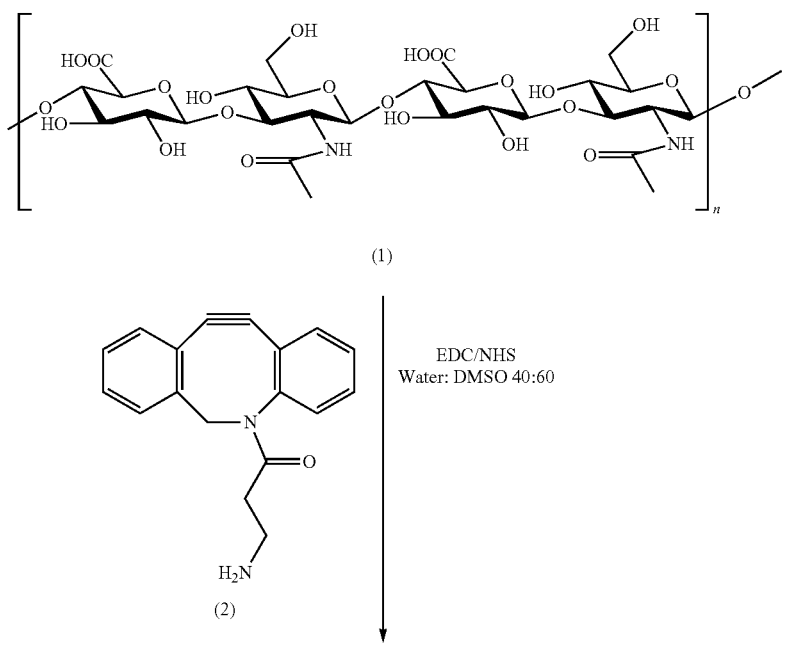

Scheme 1A

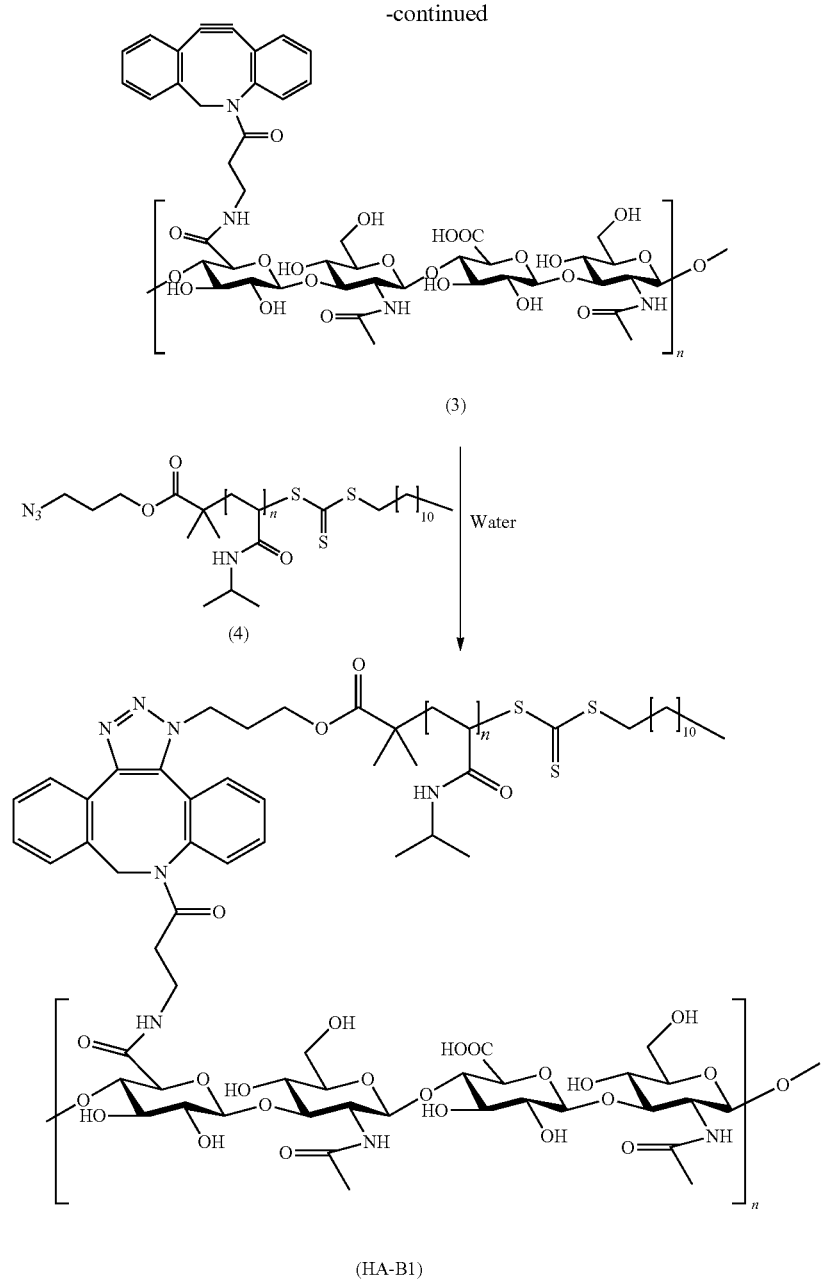

(3)

(4)

(HA-B1)

The degree of substitution (DS) of HA-DBCO was determined as 8.0% (1 eq. COO⁻) using the ratio of the integration of the DBCO aromatics protons peaks ($\delta$ 7.67 ppm) to the integration of the HA acetyl proton peak ($\delta$ 2.00 ppm) and the degree of substitution (DS) of HA-B1 was finally quantified as 7.13% (1 eq. COO⁻) using the ratio of the integration of the DBCO aromatic protons peaks ($\delta$ 7.67 ppm) to the integration of the pNiPAM methyl protons peak ($\delta$ 1.56 ppm).

Synthesis of HA-P2

The title conjugate of the invention was synthesized according to Scheme 1B below: HA (1) is solubilized in distilled water at 1% (w/v). After dissolution of the polymer, EDC was added (0.5 eq. COO⁻) and 5 min latter NHS was dissolved (0.5 eq.) under magnetic stirring (5 min at 800 RPM). The pH was adjusted to 5.0 with a pH gel electrode Metrohm (Herisau, Switzerland) with NaOH/HCl 0.1 M. DBCO-PEG4-amine (2P) was added (0.5 eq.) with DMSO for a final volume ratio 40:60 of water-DMSO mixture. The reaction was stirred overnight at room temperature and was dialyzed (MWCO 12-14,000, Spectra/Por® membrane, Rancho Dominguez, USA) against NaCl 5% (w/v) in distilled water 3 times during 3 h at 900 RPM and then in distilled water 3 times during 3 h at 900 RPM to obtain intermediate of Formula (Ib1) wherein A is a C8 heterocyloalkyl ring being dibenzocylooctyne, R⁵ is H and R³ is —C(O)—(CH₂)₂—NH—C(O)—(CH₂—CH₂—O)₄—(CH₂)₂—NH—C(O)— (3P). The mixture was re-dissolved in distilled water at 1% (w/v) and pNiPAM-N3 (0.5 eq.) (4) was added (2 h at 1,500 RPM). HA conjugates were dialyzed (MWCO 25,000, Spectra/Por® membrane, Rancho Dominguez, USA) against NaCl 5% (w/v) in distilled water 3 times during 3 h at 900 RPM and then in distilled water 3 times during 3 h at 900 RPM and lyophilized and stored at 4° C. The conjugate of the invention HA-B2 was also synthesized by this method by using DBCO-amine (2) instead of DBCO-PEG4-amine (2P) to lead to the same conjugate as (HA-B1) but with different ratios (pNiPAM/HA). After lyophilization, the structure and the DS of the obtained conjugates were determined by 1H NMR spectra in $D_2O$ as described above (FIGS. 1F and 1E). The DS of HA-B2 and HA-P2 was respectively 7.47% and 9.53% (0.5 eq. $COO^-$).

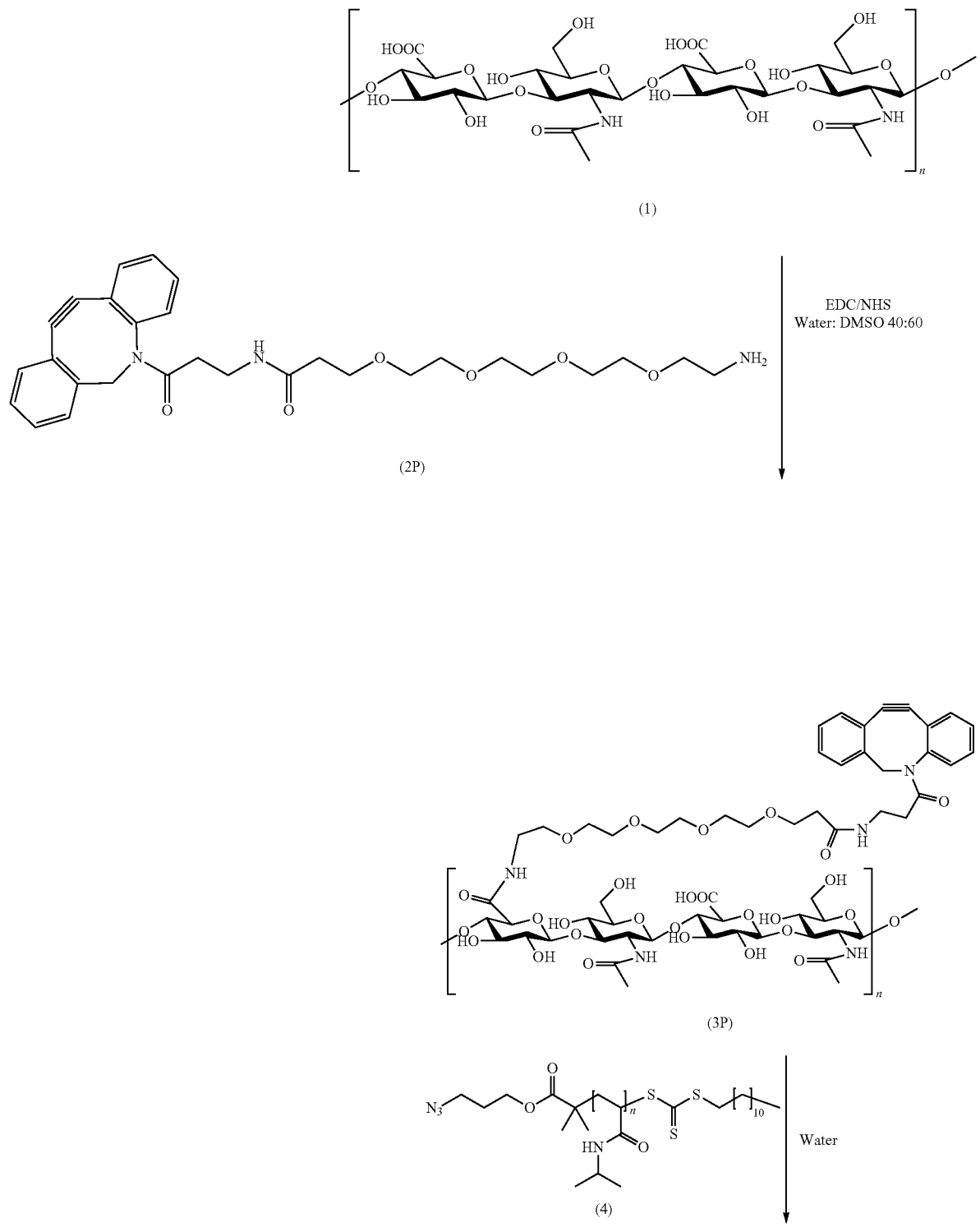

-continued
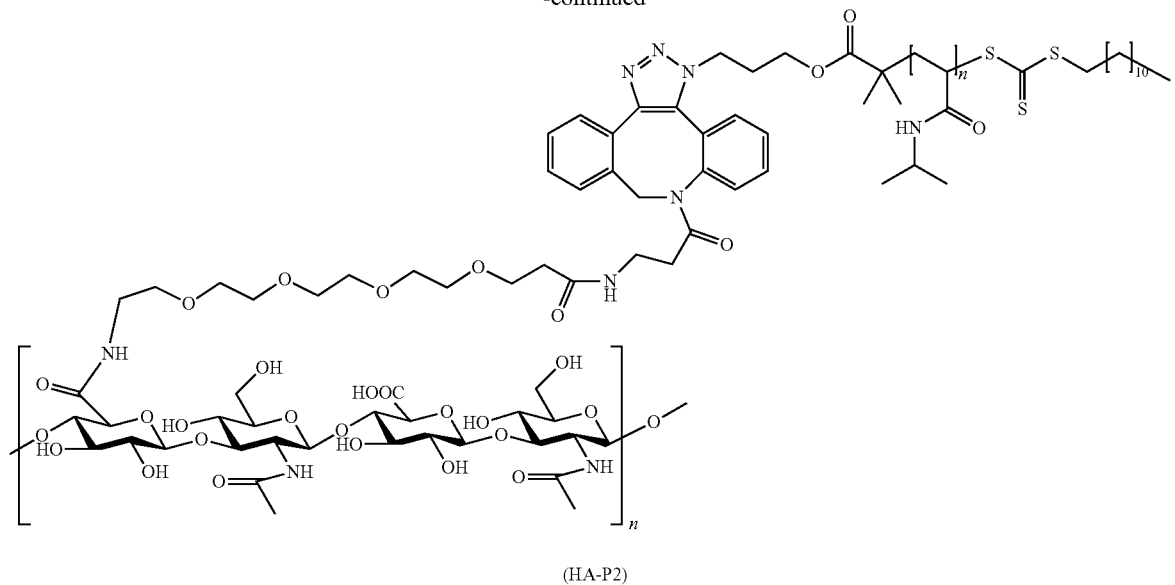
(HA-P2)
Synthesis of HA-B3
The title conjugate of the invention was synthesized according to the general Scheme 2, in particular Scheme 2A below.
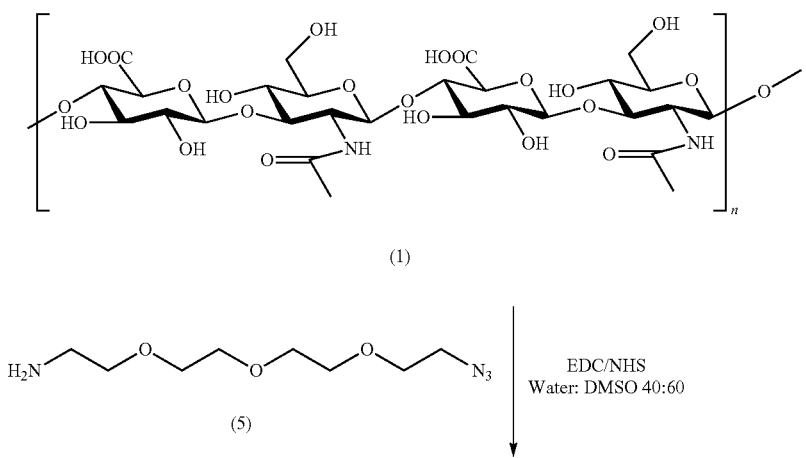

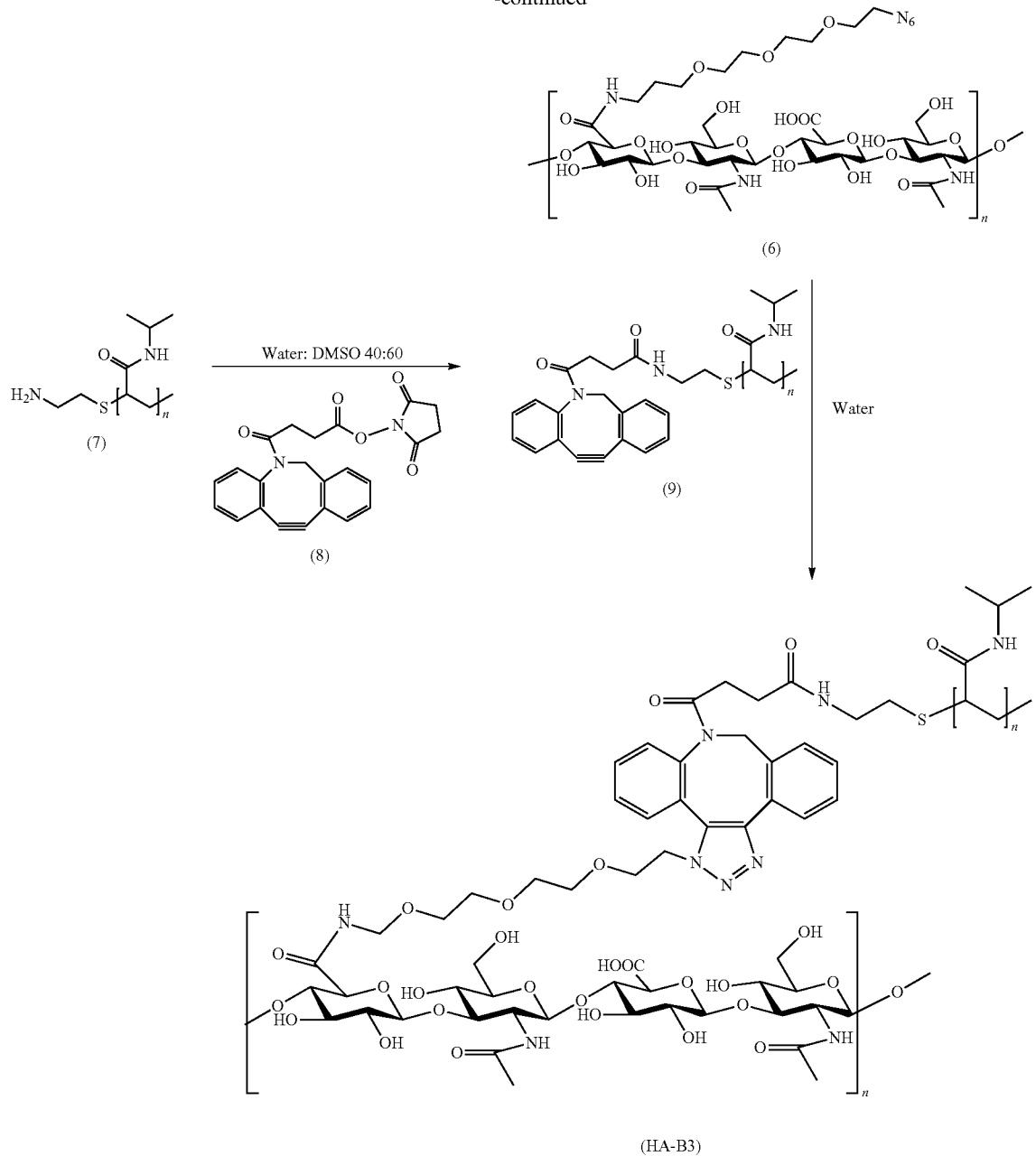

HA (1) is solubilized in distilled water at 1% (w/v). After dissolution of the polymer, EDC was added (1 eq. COO⁻) and 5 min latter NHS was dissolved (1 eq.) under magnetic stirring (5 min at 1,200 RPM). The pH was adjusted to 5.0 with a pH gel electrode Metrohm (Herisau, Switzerland) with NaOH/HCl 0.1 M and N$_3$—PEG$_4$-amine (5) was added (1 eq.) with DMSO for a final volume ratio 40:60 of water-DMSO mixture. HA-N$_3$ was dialyzed (MWCO 1,000, Spectra/Por® membrane, Rancho Dominguez, USA) against NaCl 5% (w/v) in distilled water 3 times during 3 h at 1,500 RPM and was precipitated in ethanol and lyophilized to lead to HA-N$_3$ (6) (Intermediate Ib2 wherein R$^3$ is a group —C(O)—NH—CH$_2$—O—(CH$_2$—CH$_2$—O)$_2$—CH$_2$—CH$_2$—). pNiPAM-amine (7) is dissolved in distilled water at 1% (w/v) under magnetic stirring (5 min at 1,200 RPM). The pH was adjusted to 7.0 with a pH gel electrode Metrohm (Herisau, Switzerland) with NaOH/HCl 0.1 M and DBCO-NHS Ester (8) was added (1 eq.), was used as a precursor of Formula (Lprec2) as defined above wherein A is aza-dibenzocyclooctynyl, R$^5$ is H and R1' is (2,5-dioxopyrrolidin-1-yl) 4-oxobutanoyl, with DMSO for a final volume ratio 40:60 of water-DMSO mixture to lead to pNiPAM-DBCO (9) (Intermediate Ia2 wherein A is aza-dibenzocyclooctynyl, R$^5$ is H, R$^3$ is —C(O)—(CH$_2$)$_2$—C(O)—NH—(CH$_2$)$_2$—S and R$^2$ is a group —B—(CH$_2$)$_i$-D, wherein B is absent, i is 0 and D is methyl). pNiPAM-DBCO was dialyzed (MWCO 1,000, Spectra/Por® membrane, Rancho Dominguez, USA) against distilled water 3 times during 3 h at 1,500 RPM and lyophilized.

HA-N$_3$ (6) is then solubilized in distilled water at 1% (w/v) and pNiPAM-DBCO (9) (1 eq.) was added (2 h at 1,500 RPM). HA conjugates were dialyzed (MWCO 25,000, Spectra/Por® membrane, Rancho Dominguez, USA) against NaCl 5% (w/v) in distilled water 3 times during 3 h at 900 RPM and then in distilled water 3 times during 3 h at 900 RPM and lyophilized and stored at 4° C. to lead to conjugate of the invention HA-B3, in particular a conjugate of Formula (I) wherein M is M2.

Synthesis of HA-pNiPAM (Comparative Control)

A comparative conjugate of HA-pNiPAM without linker was synthesized using the method described as follows: HA is solubilized in distilled water at 1% (w/v). After dissolution of the polymer, EDC was added (1 eq. COO−) and 5 min latter NHS was dissolved (1 eq.) under magnetic stirring (5 min at 1,200 RPM). The pH was adjusted to 5.0 with a pH gel electrode Metrohm (Herisau, Switzerland) with NaOH/HCl 0.1 M and pNiPAM-amine was added (1 eq.). The reaction was stirred overnight at room temperature. HA-pNiPAM was dialyzed (MWCO 25,000, Spectra/Por® membrane, Rancho Dominguez, USA) against NaCl 5% (w/v) in distilled water 3 times during 3 h at 1,500 RPM and was precipitated in ethanol and lyophilized and stored at 4° C.

Synthesis of HA-P2-Cy5 (Fluorescent HA Conjugate)

HA conjugates and a fluorescent dye-azide were coupled with the same synthesis parameters of HA-P2 except 0.1% (w/w) of Cy5-$N_3$, as example, was added to the mixture before the adding of pNiPAM-$N_3$.

Synthesis of HA-Cy5 (Comparative Fluorescent Control)

HA (1) is solubilized in distilled water at 1.5% (w/v). After dissolution of the polymer, EDC was added (1.1 eq. COO−) and 5 min latter NHS was dissolved (1.1 eq.) under magnetic stirring (5 min at 900 RPM). The pH was adjusted to 5.0 with a pH gel electrode Metrohm (Herisau, Switzerland) with NaOH/HCl 0.1M. DBCO-amine was added (1 eq.) with DMSO for a final volume ratio 1:1 of water-DMSO mixture. The reaction was stirred overnight at room temperature and was dialyzed (MWCO 12-14,000, Spectra/Por® membrane, Rancho Dominguez, USA) against NaCl 5% (w/v) in distilled water 3 times during 3 h at 900 RPM and then in distilled water 3 times during 3 h at 900 RPM. The mixture was re-dissolved in distilled water at 1% (w/v) and 0.1% (w/w) of Cy5-$N_3$ was added (2 h at 1,500 RPM). HA conjugates were dialyzed (MWCO 12-14,000, Spectra/Por® membrane, Rancho Dominguez, USA) against NaCl 5% (w/v) in distilled water 3 times during 3 h at 900 RPM and then in distilled water 3 times during 3 h at 900 RPM and lyophilized and stored at 4° C.

Example 2: Injectability of Compounds of the Invention

The maximal percentage (w/v) of HA conjugate below an injectable force of 5 N was determined in order to test the injectability of compounds of the invention.

Figure 2:
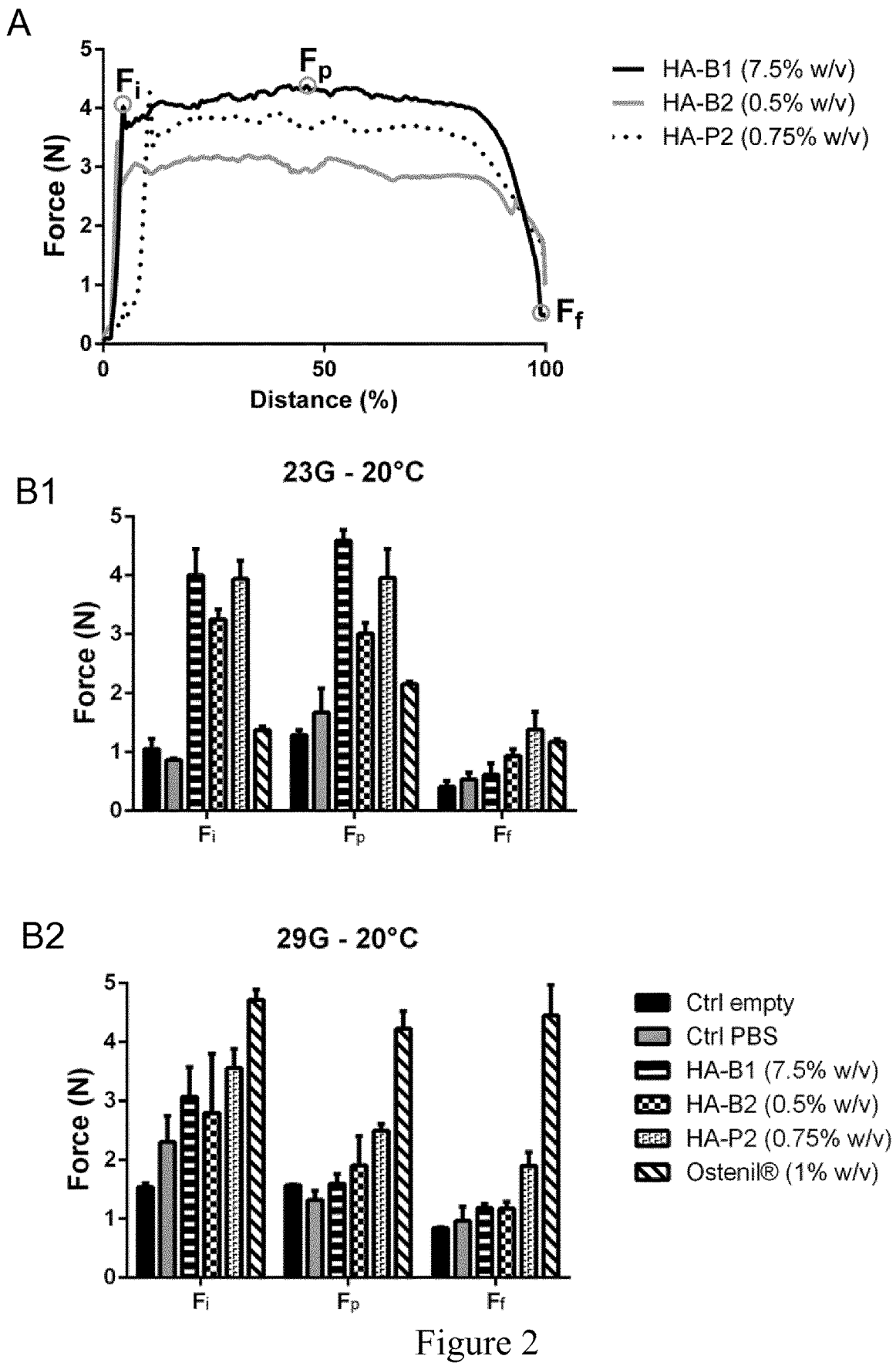
FIG. 2 shows the injectibility of graft polymers of the invention measured as described in Example 2. A: Force in Newton (N) required to expel the fluid as a function of the stroke distance of the piston in the syringe with a 23G needle (distance %). Three forces were evaluated for the characterization of the injection profile: Fi (initial force), Fp (plateau force) and Ff (final force). B: General overview of the HA graft polymers injection profiles by a 23G (B1) and 29G (B2) at 20° C. needle-syringe systems. Empty syringe, Ostenil®, and PBS were used as controls. C: General overview of the HA graft polymers injection profiles by a 29G needle at 37° C.
Figure 2:
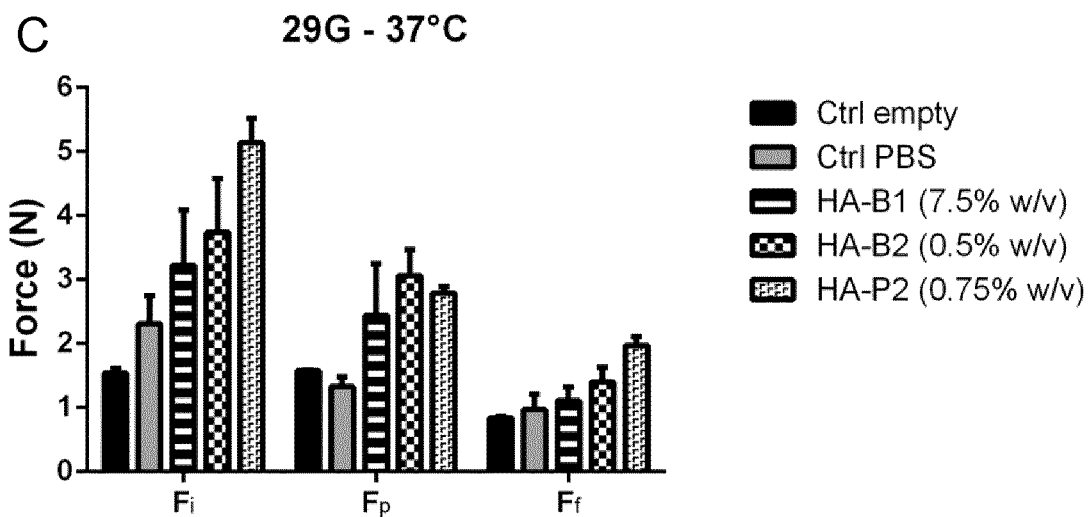

A 1 mL syringe Norm-ject® was filled with 23G needle and a BD Micro-Fine™ 29G fixed needle 1 mL insulin syringe were used. The injection force was measured at 20 and 37° C. using a Texture Analyzer TA.XT. plus (Tracomme AG, Switzerland). HA conjugates were assessed with 2 syringe-needle systems and showed an injection profile influenced by the syringe material (FIG. 2B). Indeed, BD Micro-Fine™ 29G fixed needle was made with a plunger stopper with double sealing ring for slow aspiration and injection. $F_i$ (initial force) and $F_p$ (plateau force) were similar and higher than $F_f$ (final force) with a 23G syringe and $F_i > F_p > F_f$ with a 29G syringe as shown on FIG. 2. The concentrations for HA-B1, HA-B2 and HA-P2 were respectively at 7.5%, 0.5% and 0.75% (w/v) were considered as easy to inject (<5 N). These results revealed the excellent injectability of the HA conjugates of the invention and the possible increase of the maximum concentration according to the injection system.

Example 3: Rheological Behavior of Compounds of the Invention

Rheological behavior of the compound of the invention was investigated as follows:

Rheological measurements were performed on 0.4 mL samples of HA-B1 (7.5% w/v), HA-B2 (0.5% w/v), HA-P2 (0.75% w/v) and Ostenil® (1% w/v) with a Haake Rheostress 1 using a cone-plate geometry with a 35/2° Ti cone (Vreden, Germany) and a shear rate ranging from 0.1 $s^{-1}$ to 100 $s^{-1}$ at 20° C. in a controlled humidity chamber. The results indicated that all the HA graft polymers of the invention and Ostenil® were non-newtonian and pseudoplastic fluids. The viscosity of pseudoplastic fluids decreased with the increased shearing, which is an advantageous property facilitating injection. The Lower Critical Solution Temperature (LCST) was also investigated by dynamic rheometry G' (elasticity) and G" (viscosity) moduli as a function of temperature at a heating rate of 1° C./min. LCST was characterized by the intersection of G' and G" moduli. All the HA conjugates showed a critical temperature below which the mixture was miscible (LCST): 24-25° C. for HA-P1 and 31-32° C. for HA-B2 and HA-P2. All HA graft polymers of the invention were solutions (G"<G') unlike Ostenil® and in the case of HA-P2, G' and G" values increased rapidly especially the elastic properties (G'), unlike HA-B1. The grafting of pNiPAM and the linker influenced the nanoparticles formation and in turn changed the rheological properties above the LCST indicating a biphasic nanoparticles-solvent mixture.

Example 4: Size and Morphology of Particle of Conjugates of the Invention

HA graft polymers of the invention were solubilized in distilled water and the HA graft polymers solutions were incubated at 37° C., thus forming nanoparticles.

Figure 3:
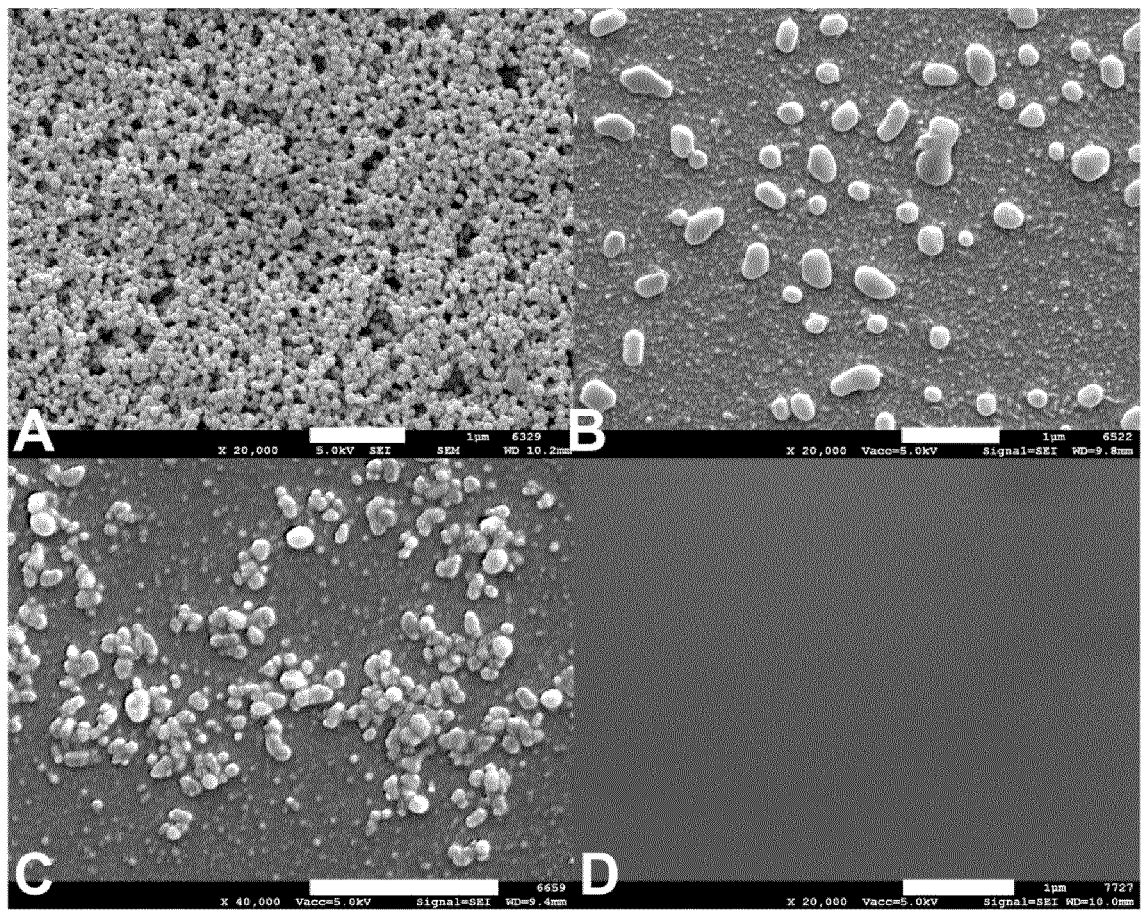
FIG. 3 shows SEM micrographs of HA-B1 (A), HA-B2 (B), HA-P2 (C) and HA-pNiPAM graft polymer (negative control) (D). Scale bar=1 µm and the percentage of nanoparticles formed as function of the temperature (from 40 to 25° C., 3 min/step) measured by Nanoparticle Tracking Analysis (E) measured as described in Example 4.
Figure 3:
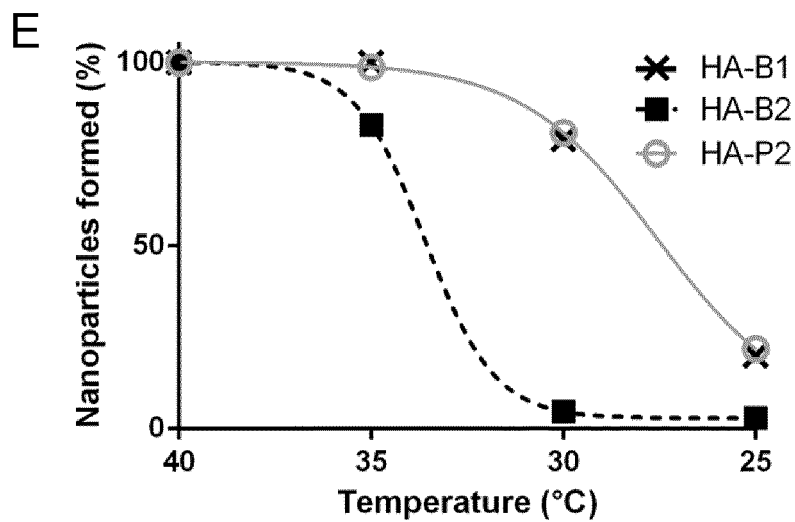

The mean particles size of the so-formed HA nanoparticles were determined above the LCST by three methods: Scanning electron microscopy (SEM) (Jeol Microscope, JSM-7001TA, Tokyo, Japan) micrographs by measuring the diameters of 50 particles using Image J version 1.45s analysis software (NIH, USA), Dynamic Light Scattering (DLS) (Nanosizer, Malvern, England) and Nanoparticle Tracking Analysis (NTA) (NanoSight LM10, Malvern, England). SEM analysis revealed the nanoparticle morphologies of the HA conjugates after incubation at 37° C. as shown on FIG. 3. The HA-B1 nanoparticles were smaller and very spherical compared to the other HA conjugates. The high grafting ratio of pNiPAM/HA influenced the spherical formation (FIG. 3 ABC) of the nanoparticles and also the viscosity/elasticity as function of the temperature. For HA-P2 (FIG. 3B), the nanoparticle size indicated the influence of the PEG4 linker. Also, HA-P2 nanoparticles were slowly re-solubilized below the LCST (31-32° C.) unlike the fast reversible transition of HA-B2 (FIG. 3E). Distinctly, the PEG4 linker influenced the solubility of the HA conjugates and the nanoparticles size formed (Table 1).

TABLE 1

| Conjugate of the invention | SEM - Size mode in number (nm) | DLS - size in intensity (nm) | NTA - size in number (nm) |
| --- | --- | --- | --- |
| HA-B1 | 88-97 | 223 ± 55 | 52 |
| HA-B2 | 65-84 | 133 ± 24 | 53 |
| HA-P2 | 203-261; 377-435 | 239 ± 95 | 231 |

In contrast, Ostenil® hydrogel and graft polymer HA-pNiPAM without linker (negative control) (FIG. 3D) did not form nanoparticles at all upon heating.

Example 5: Intravital Fluorescence

The in vivo residence time of conjugates of the invention was assessed as follows: Intravital fluorescence in mice was assessed for HA-P2-Cy5 and HA-Cy5 (comparative control) after administration by two injection routes in mice (healthy hypodermis and intra-articular injection in knee osteoarthritis). HA-P2-Cy5 and HA-Cy5 solutions (1% w/v) were injected into joints (n=7) and in subcutaneous (n=4).

Figure 5:
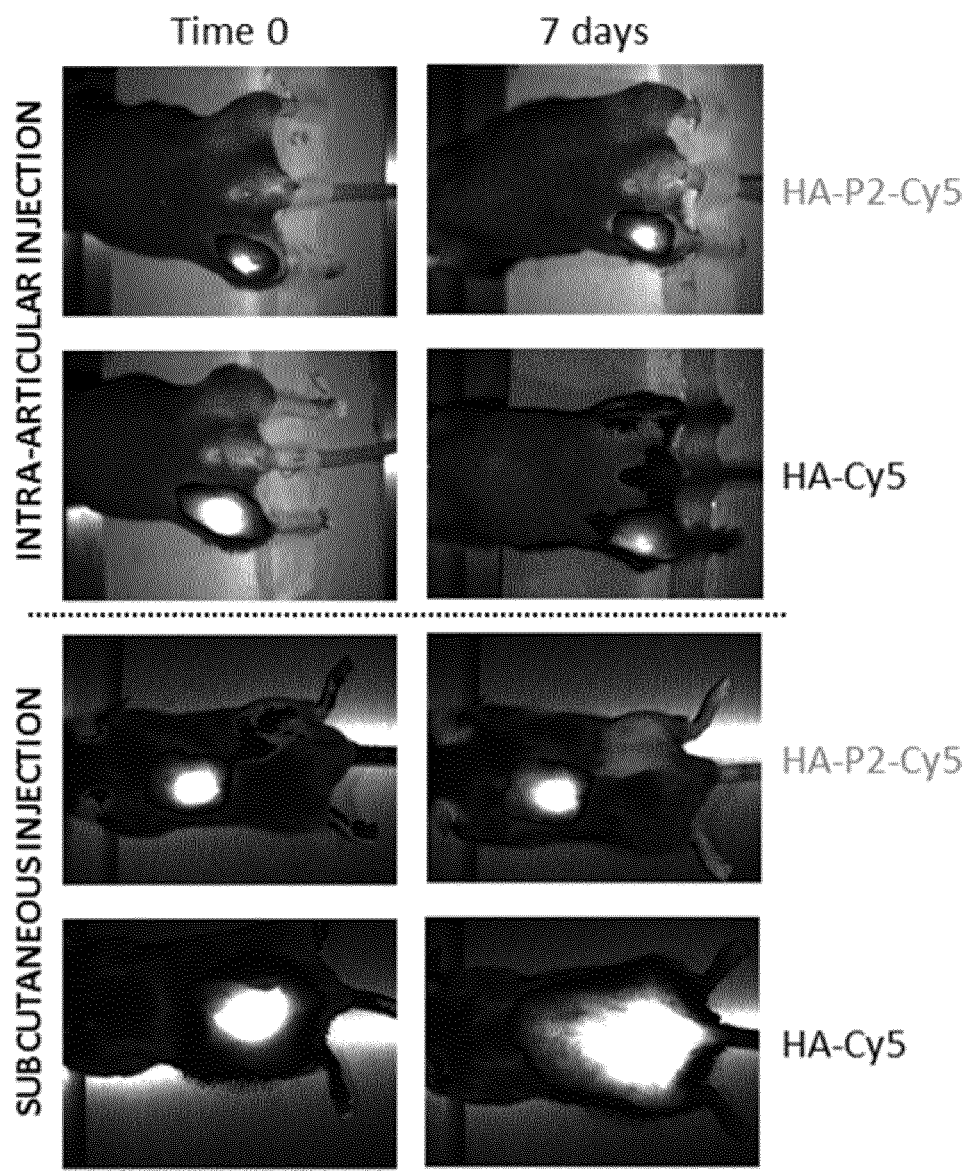
FIG. 5 shows examples of increased residence/persistence of HA-Cy5 and HA-P2-Cy5 intravital fluorescence superimposed with white light images in mice after subcutaneous injection in healthy mice and intra-articular injection for 7 days in osteoarthritis mice model as described in Example 5.

In the case of HA-Cy5 significant differences were observed. After 7 days the total signal decreased in intra-articular injection and the area in pixels increased for the subcutaneous site. HA-Cy5 showed a short residence time at the injection site (FIG. 5). HA-P2-Cy5 spontaneously formed nanoparticles at body temperature. The increase of area in pixels was balanced by the decrease of the average signal. Clearly, no significant differences for the total signal of HA-P2-Cy5 were found The HA conjugate showed a long residence time in the body at the injection site due to the spontaneous nanoparticles formation (FIG. 5).

Example 6: Biocompatibility

The biocompatibility of conjugates of the invention was assessed as follows: After 7 days (n=4) and 21 days (n=4) subcutaneous injection in healthy mice of HA-P2-Cy5, pieces of skins were removed, where the Cyanine 5 fluorescence was detected, and were cut in the sagittal plane. After embedding in paraffin, 4 μm sections were cut with a microtome. Sections were stained with hematoxylin-eosin (HE). The biocompatibility of HA-P2-Cy5 at injection sites is controlled by the tissue/material interaction. Interaction and biocompatibility of HA-P2-Cy5 in subcutaneous injection after 21 days was confirmed. Macrophages, major cells in the tissue reaction were not more in surrounding tissues compared to the control group (Ostenil®).

Example 7: In Vitro Drug Release

To determine the drug release profile from nanoparticles from HA graft polymers of the invention, in vitro drug release was conducted as follows. Saline solution (NaCl 0.9%), Ostenil®, graft polymers of the invention HA-B2 and HA-P2 were saturated by dexamethasone base (drug). Ten mL of the previous solutions were placed in a dialysis bag (MWCO 1,000, Spectra/Por® membrane, Rancho Dominguez, USA) against 400 mL NaCl 0.9% (w/v) and incubated at 37° C. and 80 RPM. After 28 h, polymer matrix was hydrolyzed by heating (121° C.) releasing their remaining content of dexamethasone and DMSO was added to a final volume ratio 1:1 water:DMSO. Drug released at each time point was quantified by reversed-phase UHPLC using a C18 Hypersil Gold column (50/2.1, 1.9 μm bead particle size, Thermo Scientific, Waltham, USA). The mobile phase comprised of 0.1% v/v formic acid in water (A) and 0.1% v/v trifluoroacetic acid (TFA) in acetonitrile (B) and a gradient elution was used with 30-95% A (0-3 min), 95-10% A (3-4 min), 10-30% A (4-4.5 min) and 30% A (4.5-5 min), at a flow rate of 400 $\mu L \cdot min^{-1}$.

Figure 4:
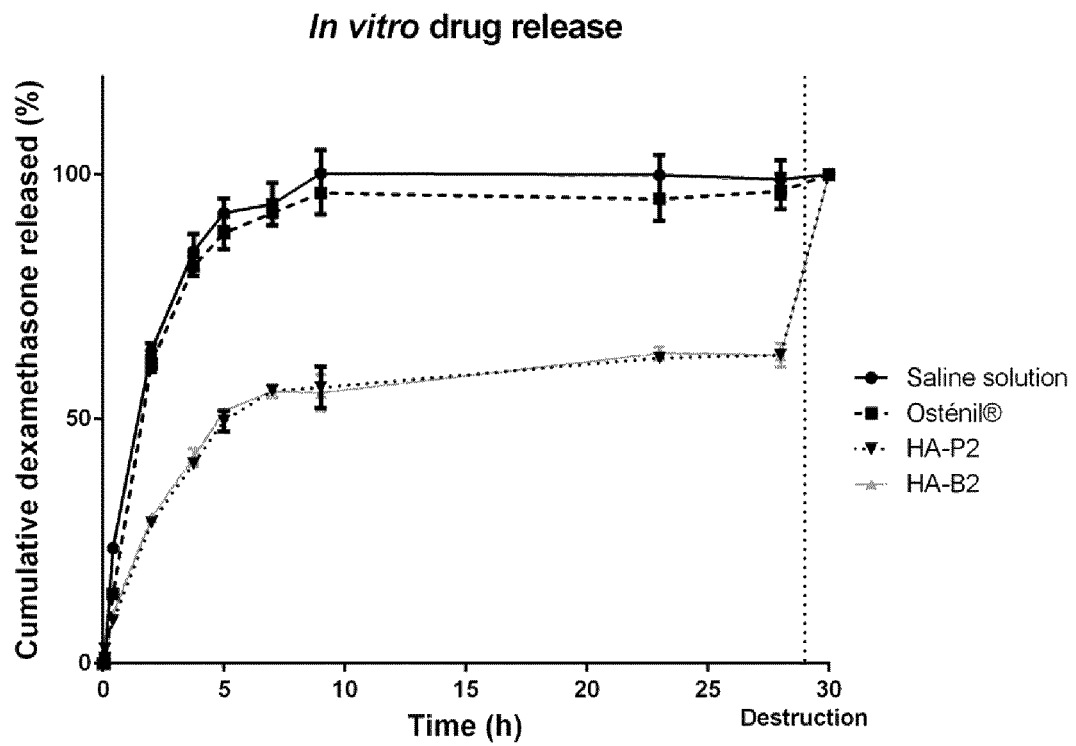
FIG. 4 shows the cumulative in vitro drug release profile of dexamethasone from the saline solution, Ostenil®, HA-B2 and HA-P2 at 37° C. as described in Example 7. After 28 h, polymer matrix was hydrolyzed by heating (121° C.), and the remaining content of dexamethasone was measured.

HA graft polymers took up about 2.5 times more dexamethasone compared to the controls (saline solution and Ostenil®). As shown in FIG. 4, after destruction (t=30 h) 40% of dexamethasone was still inside the nanoparticles of HA conjugates.

Above the LCST, HA conjugates nanoparticles were loaded with hydrophobic drug substance as dexamethasone base. This study demonstrated the high efficiency of HA conjugates nanoparticles of the invention as a new drug delivery system.

Example 8: Stability

The stability of graft polymers of the invention was assessed by rheology and pH/zeta potential measurements as follows:

HA graft polymers were stored at 4° C. and the viscosity was checked over time ($t_0$, $t_7$ and $t_{30}$). Rheological measurements were performed on 0.4 mL samples of HA-B2 (0.5% w/v) and HA-P2 (0.75% w/v) with a Haake Rheostress 1 using a cone-plate geometry with a 35/2° Ti cone (Vreden, Germany) and a logarithmic shear rate mode ranging from 0.1 $s^{-1}$ to 100 $s^{-1}$ at 20° C. in a controlled humidity chamber. The pH was measured with a pH gel electrode Metrohm (Herisau, Switzerland) and Zeta potential was measured using a Zetasizer NanoZS (Malvern, Worcestershire, UK).

No significant viscosity differences were observed, indicating that graft polymers HA-B2 and HA-P2 were stable for 1 month at 4° C. HA graft polymers showed an acid pH with high zeta potential, ensuring colloidal stability (Table 2). In order to neutralize the pH, the HA graft polymers s were solubilized in phosphate-buffered saline (PBS) for in vitro/in vivo experiments.

TABLE 2

|  | pH | Zeta potential [mV] |
| --- | --- | --- |
| HA-B1 7.5% (w/v) | 6.38 | −30.7 ± 2.5 |
| HA-B2 0.5% (w/v) | 5.64 | −28.5 ± 1.2 |
| HA-P2 0.75% (w/v) | 5.73 | −32.6 ± 1.6 |
| Ostenil ® (1% w/v) (buffered) | 6.99 | −34.5 ± 4.0 |

Example 9: Cell Viability Assay

Viability tests were performed using human synovial fibroblasts. The cells were plated at a density of 20,000 cells/well in 96-well plates. After 24 h, HA conjugates (HA-B2 and HA-P2) were solubilized in PBS and were incubated for 24 h at 37° C. 50 μL of 0.5% MTT solution was added to each well for 3 h. All wells were incubated for 45 min with 100 μL of DMSO and the absorbance was measured at 570 nm (8 points per well) by BioTeK Synergy Mx (Winooski, USA).

HA-B2 0.75% (w/v) and HA-P2 0.5% (w/v) in PBS did not decrease cells viability compared to untreated controls.

optionally substituted aminocarbonyl $C_1$-$C_6$ alkyl and optionally substituted $C_1$-$C_6$ alkoxy and $L_1$ is selected from —$NR^{10}C(O)$—, —$C(O)$—$NR^{10}$—, —$C(O)$—O— and —$C(O)$— wherein $R^9$ and $R^{10}$ are independently selected from H and optionally substituted $C_1$-$C_6$ alkyl; A is an optionally substituted $C_5$-$C_{10}$-cycloalkyl, or optionally substituted heterocycloalkyl ring wherein $R^5$ represents one or more substituent(s) independently selected from H, optionally substituted alkoxy and optionally substituted $C_1$-$C_6$ alkyl; x, y and z are integers independently selected from 1 to 20 or any pharmaceutically acceptable salts thereof.

2. The graft polymer according to claim 1 of Formula (I):

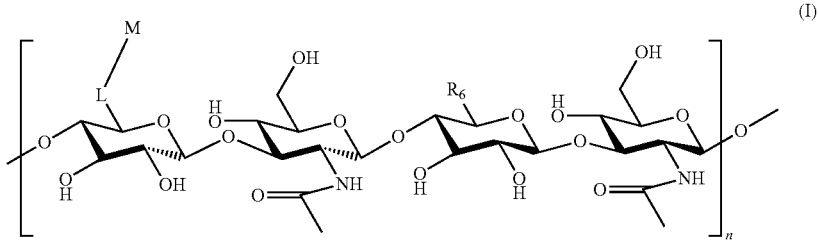

The invention claimed is:

1. A graft polymer of a hyaluronic acid polymer and a N-isopropylacrylamide based polymer wherein the hyaluronic acid polymer and the N-isopropylacrylamide based are conjugated through at least one linker L of Formula (II):

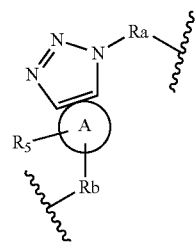

wherein one of Ra and Rb is covalently linked to the N-isopropylacrylamide based polymer and one of Ra and Rb is covalently linked to the hyaluronic acid polymer and when Ra or Rb is covalently linked to the N-isopropylacrylamide based polymer, it is equal to $R^1$ and when Ra or Rb is covalently linked to the hyaluronic acid polymer, it is equal to $R^3$, wherein $R^1$ is a group selected from $(CH_2)_x$—$NH(CH_2)_y$—S—, —$(CH_2)_x$—$NH$—O—$C(O)$—$(CH_2)_y$—S—, —$(CH_2)_x$—$NH$—$(CH_2)_y$—$C(O)$—$NH$—$(CH_2)_z$—S—, —$(CH_2)_x$—O—$C(O)$—$CR^7R^8$—, —$C(O)$—$(CH_2)_x$—$C(O)$—$NH$—$(CH_2)_z$—S and an optionally substituted polyethylene chain wherein $R^7$ and $R^8$ are optionally substituted $C_1$-$C_6$ alkyl; $R^3$ is a group -E-G-$L_1$- wherein E is either absent or selected from —$C(O)$—$NR^9$—, —$C(O)$—O— and —$C(O)$—, G is linker group selected from optionally substituted $C_1$-$C_{20}$ alkyl, optionally substituted polyethylene glycol (PEG) chain, optionally substituted acylamino $C_1$-$C_6$ alkyl, optionally substituted acyl $C_1$-$C_6$ alkyl, wherein M is a group selected from a moiety of Formula (M1) and of Formula (M2):

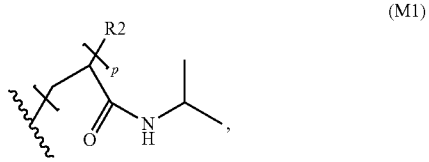

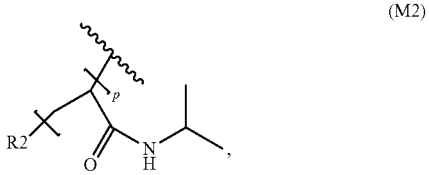

$R^2$ is a group —B—$(CH_2)_i$-D, wherein B is either absent or selected from —S—$C(S)$—S— and —S—; D is a group selected from optionally substituted $C_1$-$C_{15}$ alkyl, optionally substituted alkoxycarbonyl $C_1$-$C_4$ alkyl, optionally substituted amino $C_1$-$C_4$ alkyl, optionally substituted aminocarbonyl $C_1$-$C_6$ alkyl, —COOH and —$NH_2$; p is an integer independently selected from 1 to 500; i is an integer independently selected from 0 to 500; $R^6$ is a group selected from —COOH and $R^3$, depending on the degree of substitution; L is a linker of Formula (II) as defined in claim 1 and n is an integer selected from 1 to 7,000 or any pharmaceutically acceptable salts thereof.

3. The graft polymer according to claim 1, having a Formula (Ia):

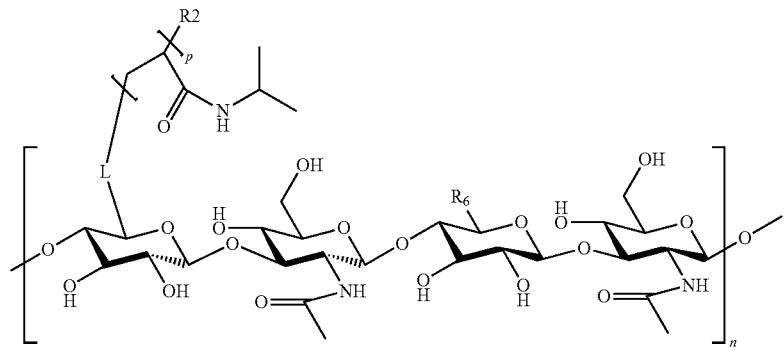

(Ia)

or any pharmaceutically acceptable salts thereof wherein L is a linker as defined in claim 1; $R^2$ is a group —B—$(CH_2)_i$-D, wherein B is either absent or selected from —S—C(S)—S— and —S—; $R^6$ is a group selected from —COOH and $R^3$, depending on the degree of substitution and p is an integer independently selected from 1 to 500.

4. The graft polymer according to claim 1, wherein the linker L is linked to the HA polymer of the graft polymer through its $R_b$ substituent.

5. The graft polymer according to claim 1, wherein the linker L is linked to the HA polymer of the graft polymer through its $R_a$ substituent.

6. The graft polymer according to claim 1, wherein x is from 2 to 10.

7. The graft polymer according to claim 1, wherein B is absent or —S—C(S)—S—.

8. The graft polymer according to claim 1, wherein L is a group according to Formula (II'):

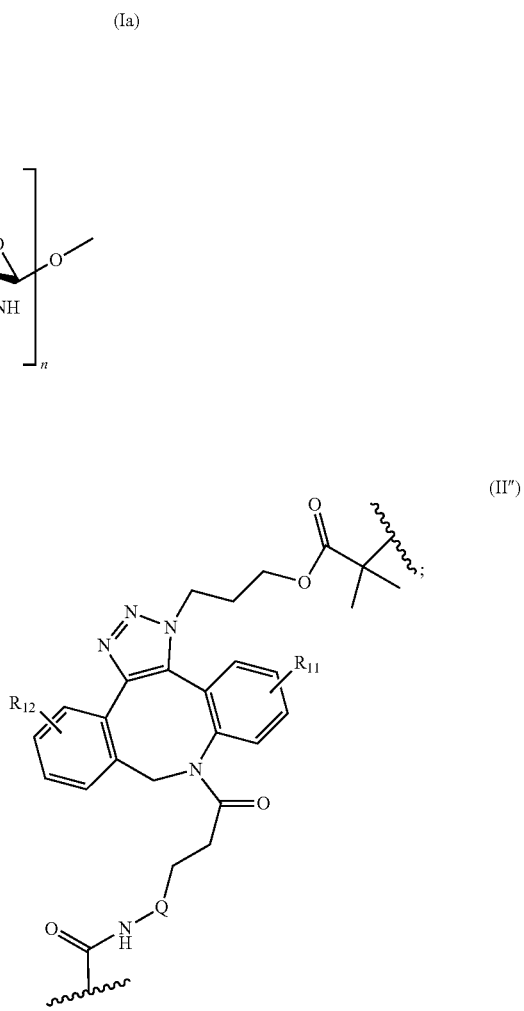

wherein $R^{11}$ and $R^{12}$ represent one or more substituent independently selected from H, optionally substituted alkoxy and optionally substituted $C_1$-$C_4$ alkyl; $R_a$ and $R_b$ are as described in claim 1.

9. The graft polymer according to claim 1, wherein L is a group according to Formulae (II) having a formula selected from Formula (II") and (II'''):

wherein Q is absent or a group of the following formula:
—NH—C(O)—$(CH_2$—$CH_2$—O$)_{1-4}$—$CH_2$—$CH_2$—;
$G_1$ is a PEG, in particular $(CH_2$—$CH_2$—O$)_{1-4}$— and $R^{11}$ and $R^{12}$ represent one or more substituent independently selected from H, optionally substituted alkoxy and optionally substituted $C_1$-$C_4$ alkyl.

10. The graft polymer according to claim 1, wherein said graft polymer is selected from the following group:

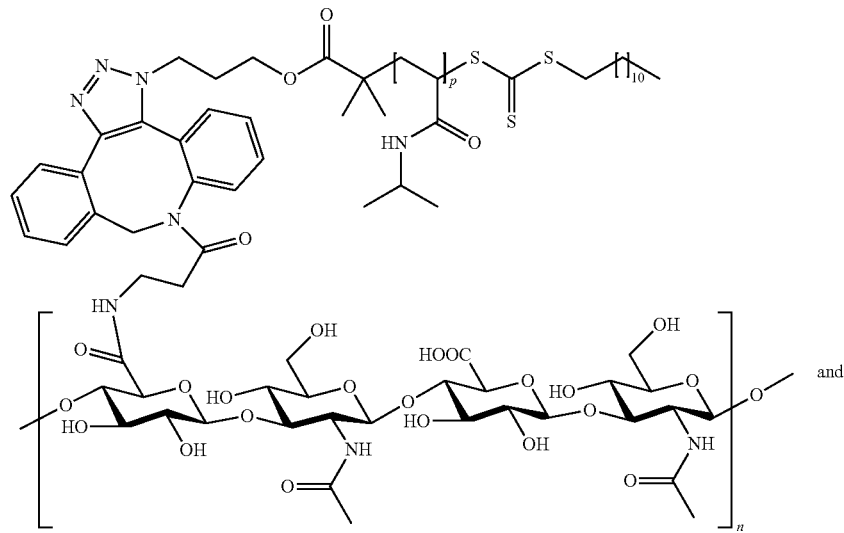
(HA-B1/HA-B2)
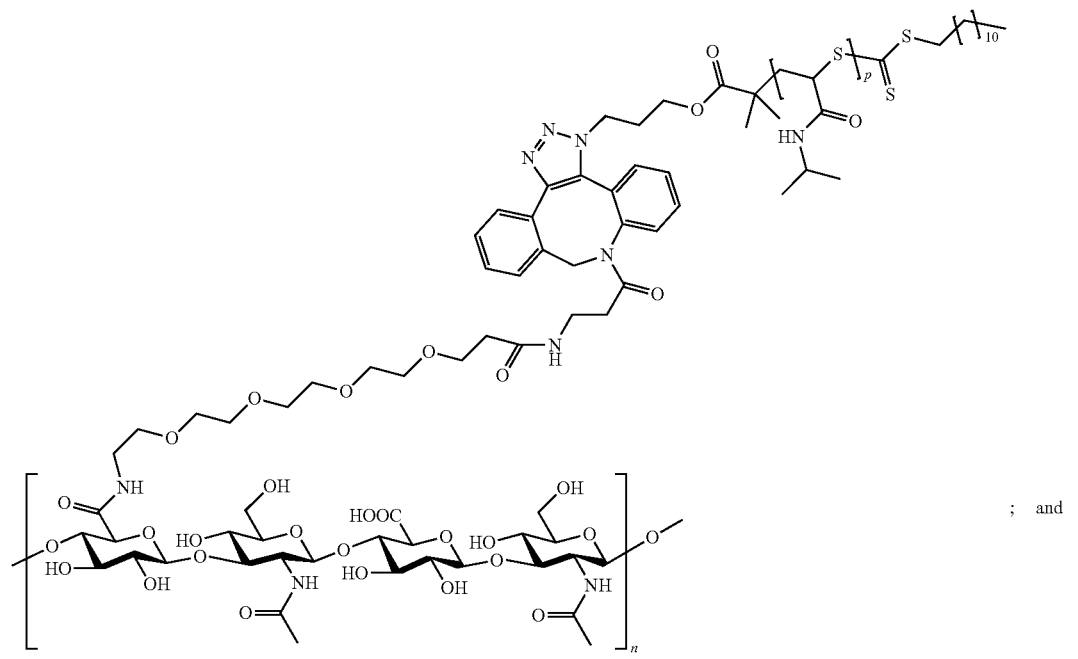
(HA-P2)
; and

-continued

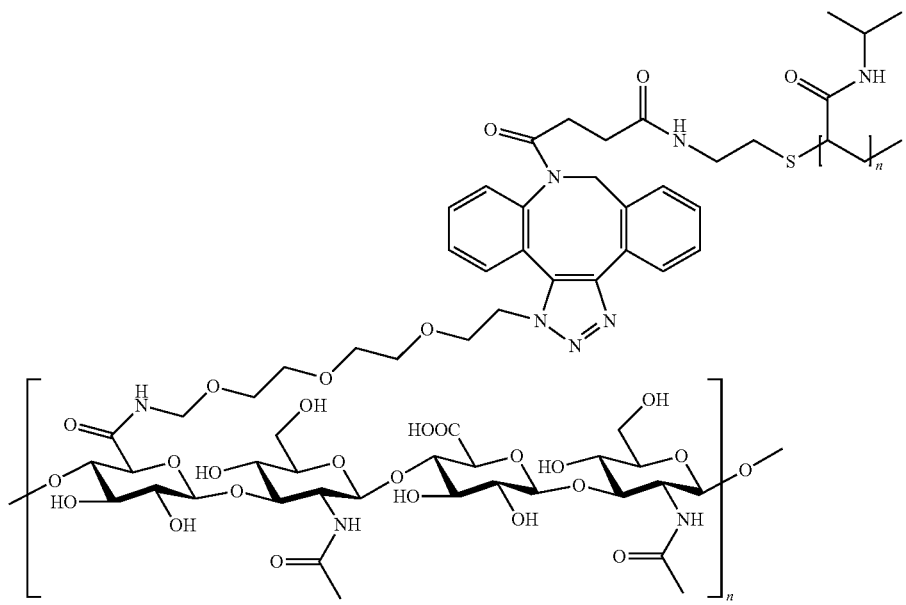

(HA-B3)

having a substitution degree between about 0.5 and 50 or any pharmaceutically acceptable salts thereof.

11. A method for the preparation of a graft polymer of a hyaluronic acid polymer and N-isopropylacrylamide based polymer wherein the hyaluronic acid polymer and the N-isopropylacrylamide based are conjugated by at least one linker L of Formula (II)

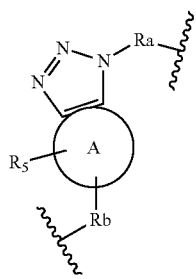

(II)

wherein A, Ra, Rb and R5 are as defined in claim 1, comprising the steps of:
(a) providing an HA polymer having at least one carboxylic acid group which is conjugated to at least one first functional group capable of participating in a "click chemistry" reaction;
(b) providing a N-isopropylacrylamide based polymer having at least one-second complementary functional group capable of participating in a "click chemistry" reaction with the first functional group wherein said one of the functional groups is an azide moiety and the other functional group is an alkyne-bearing precursor of the said linker L;
(c) reacting the at least one first functional group of the HA polysaccharide with the at least one-second complementary functional group of the N-isopropylacrylamide based polymer via a "click chemistry"

reaction to obtain a graft polymer composition of the invention; and
(d) isolating the graft polymer composition.

12. A composition comprising at least one graft polymer according to claim 1 and at least one carrier.

13. The composition according to claim 12, wherein said composition is a hydrogel or nanoparticle composition.

14. The composition according to claim 12, wherein said composition is a cell or tissue culture medium further comprising cell or tissue nutrients.

15. The composition according to claim 12, wherein said composition is a reconstruction tissue.

16. The composition according to claim 12, wherein said composition is a cosmetic composition and the said carrier is a cosmetically acceptable carrier.

17. A soft tissue filler comprising at least one graft polymer according to a graft polymer according to claim 1.

18. A method for the preparation of a delivery system of an active principle, said method comprising the steps of:
a) Providing a graft polymer or hydrogel according to claim 1 in gel state;
b) Providing an active principle to be delivered;
c) Mixing the said graft polymer composition or hydrogel with the said active principle;
d) Optionally inducing formation of nanoparticles by increasing the temperature to the mixture; and
e) Collecting the obtained composition, hydrogel or nanoparticles loaded with the active principle.

19. A method of preventing, treating or ameliorating a medical disorder selected from joint pathologies, articular diseases, eye pathologies, skin defects or injuries, urological tissue bulking and any tissue degeneration, a tumor or a vascular malformation in a subject, said method comprising administering to a subject in need thereof an effective amount of at least one HA graft polymer according to claim 1 or a pharmaceutical formulation thereof.

20. The composition according to claim 12, wherein the carrier is a pharmaceutically acceptable carrier.

21. A method of preparing a cell or tissue culture medium comprising mixing at least one HA graft polymer according to claim 1 with cell or tissue culture medium.

22. A method of preparing a material for tissue engineering comprising mixing at least one HA graft polymer according to claim 1 with a tissue engineering material.

23. The method according to claim 22, wherein the tissue engineering material is bone, cartilage, epidermal material or cells.

24. A method of preparing a composition comprising mixing at least one HA graft polymer according to claim 1 with a carrier.

\* \* \* \* \*